United States Patent
Cho et al.

(10) Patent No.: US 11,628,206 B2
(45) Date of Patent: Apr. 18, 2023

(54) METHOD FOR INHIBITING STAT3 ACTIVITY COMPRISING ADMINISTERING SSU72

(71) Applicant: CUROGEN TECHNOLOGY CO., LTD., Suwon-si (KR)

(72) Inventors: Mi-La Cho, Seoul (KR); Sung-Hwan Park, Seoul (KR); Seung-Ki Kwok, Seoul (KR); Jong-Young Choi, Seoul (KR); Seung-Hun Lee, Gwacheon-si (KR); Hyeon-Beom Seo, Seoul (KR); Young-Mee Moon, Seoul (KR); Jin-Sil Park, Seoul (KR); Min-Jung Park, Seoul (KR); Jin-Kwan Lee, Suwon-si (KR); Chang Woo Lee, Suwon-si (KR)

(73) Assignee: CUROGEN TECHNOLOGY CO., LTD., Suwon-si (KR)

( * ) Notice: Subject to any disclaimer, the term of this patent is extended or adjusted under 35 U.S.C. 154(b) by 50 days.

(21) Appl. No.: 17/154,924

(22) Filed: Jan. 21, 2021

(65) Prior Publication Data
US 2021/0220447 A1 Jul. 22, 2021

Related U.S. Application Data

(63) Continuation of application No. 15/563,435, filed as application No. PCT/KR2016/003352 on Mar. 31, 2016, now Pat. No. 10,925,933.

(30) Foreign Application Priority Data

Mar. 31, 2015 (KR) .................. 10-2015-0045114
Mar. 31, 2016 (KR) .................. 10-2016-0038934

(51) Int. Cl.
| | | |
|---|---|---|
| *A61P 7/00* | (2006.01) |
| *A61K 38/46* | (2006.01) |
| *A61P 27/02* | (2006.01) |
| *A61P 17/06* | (2006.01) |
| *A61P 3/08* | (2006.01) |
| *A61P 25/28* | (2006.01) |
| *A61P 3/00* | (2006.01) |
| *A61P 37/06* | (2006.01) |
| *A61P 1/18* | (2006.01) |
| *A61P 3/04* | (2006.01) |
| *A61P 17/00* | (2006.01) |
| *A61P 19/02* | (2006.01) |
| *A61P 19/10* | (2006.01) |
| *C12N 7/00* | (2006.01) |
| *C12Q 1/686* | (2018.01) |
| *G01N 33/50* | (2006.01) |

(52) U.S. Cl.
CPC .............. *A61K 38/465* (2013.01); *A61P 1/18* (2018.01); *A61P 3/00* (2018.01); *A61P 3/04* (2018.01); *A61P 3/08* (2018.01); *A61P 7/00* (2018.01); *A61P 17/00* (2018.01); *A61P 17/06* (2018.01); *A61P 19/02* (2018.01); *A61P 19/10* (2018.01); *A61P 25/28* (2018.01); *A61P 27/02* (2018.01); *A61P 37/06* (2018.01); *C12N 7/00* (2013.01); *C12Q 1/686* (2013.01); *C12Y 301/03016* (2013.01); *G01N 33/5041* (2013.01); *C12N 2710/16143* (2013.01)

(58) Field of Classification Search
None
See application file for complete search history.

(56) References Cited

U.S. PATENT DOCUMENTS

2015/0050288 A1   2/2015   Pardoll et al.

OTHER PUBLICATIONS

Bellemore, S.M., et al. Clin and Exp. Immunol. 182:261-269 (Year: 2015).
Zhang, L, et al. FLOS One. 6(12):1-11 (Year: 2011).
McGeachy, M., et al. Nat. Immunol. 8(12):1390-1397 (Year: 2007).
Werner-Allen, Jon W. et al., "cis-Proline-mediated Ser(P)5 Dephosphorylation by the RNA Polymerase II C-terminal Domain Phosphatase Ssu72*," The Journal of Biological Chemistry, 1 vol. 286, No. 7, pp. 5717-5726, Feb. 18, 2011.
Ganem, Carine et al., "Ssu72 is a phosphatase essential for transcription termination of snoRNAs and specific mRNAs n yeast," The EMBO Journal, vol. 22, No. 7, pp. 1588-1598, 2003.
Darnell JE Jr., "STATs and gene regulation," Science, vol. 277, No. 5332, pp. 1630-1635, Sep. 12, 1997.
Bromberg JF et al., "Stat3 as an oncogene," Cell, vol. 98, No. 3, pp. 295-303, Aug. 6, 1999.
Vera J et al., "Systems biology of JAK-STAT signalling in human malignancies," Progress in Biophysics & Molecular Biology, vol. 106, No. 2, pp. 426-434, Aug. 2011, DOI: 10.1016/j.pbiomolbio.2011.06.013.
Turkson J, "STAT proteins as novel targets for cancer drug discovery," Expert Opinion on Therapeutic Targets, vol. 8, No. 5, pp. 409-422, Oct. 2004.
Duan FI et al., "Functional long-range interactions of the IgFl 3' enhancers with the bcl-2 promoter region in t(14;18) lymphoma cells," Oncogene, vol. 27, No. 53, pp. 6720-6728, Dec. 4, 2008, DOI: 10.1038/onc.2008.286.

*Primary Examiner* — G. R. Ewoldt
(74) *Attorney, Agent, or Firm* — Sughrue Mion, PLLC

(57) ABSTRACT

The present disclosure relates to a method for inhibiting a STAT3 activity comprising administering SSu72 protein.

3 Claims, 26 Drawing Sheets

Specification includes a Sequence Listing.

flow cytometry *ex vivo*-spleen flow cytometry *ex vivo*-lymph node

SEQUENCE LISTING

<160> NUMBER OF SEQ ID NOS: 17

<210> SEQ ID NO 1
<211> LENGTH: 194
<212> TYPE: PRT
<213> ORGANISM: Homo sapience

<400> SEQUENCE: 1

```
Met Pro Ser Ser Pro Leu Arg Val Ala Val Cys Ser Ser Asn Gln
1               5                   10                  15

Asn Arg Ser Met Glu Ala His Asn Ile Leu Ser Lys Arg Gly Phe Ser
                20                  25                  30

Val Arg Ser Phe Gly Thr Gly Thr His Val Lys Leu Pro Gly Pro Ala
                35                  40                  45

Pro Asp Lys Pro Asn Val Tyr Asp Phe Lys Thr Thr Tyr Asp Gln Met
        50                  55                  60

Tyr Asn Asp Leu Leu Arg Lys Asp Lys Glu Leu Tyr Thr Gln Asn Gly
65                  70                  75                  80

Ile Leu His Met Leu Asp Arg Asn Lys Arg Ile Lys Pro Arg Pro Glu
                85                  90                  95

Arg Phe Gln Asn Cys Thr Asp Leu Phe Asp Leu Ile Leu Thr Cys Glu
                100                 105                 110

Glu Arg Val Tyr Asp Gln Val Val Glu Asp Leu Asn Ser Arg Glu Gln
            115                 120                 125

Glu Thr Cys Gln Pro Val His Val Val Asn Val Asp Ile Gln Asp Asn
        130                 135                 140

His Glu Glu Ala Thr Leu Gly Ala Phe Leu Ile Cys Glu Leu Cys Gln
145                 150                 155                 160

Cys Ile Gln His Thr Glu Asp Met Glu Asn Glu Ile Asp Glu Leu Leu
                165                 170                 175

Gln Glu Phe Glu Glu Lys Ser Gly Arg Ala Phe Leu His Thr Val Cys
                180                 185                 190

Phe Tyr
```

<210> SEQ ID NO 2
<211> LENGTH: 1319
<212> TYPE: DNA
<213> ORGANISM: Homo sapience

<400> SEQUENCE: 2

| | | | | |
|---|---|---|---|---|
| gacgccgccg | cttggcgccg | tgacgctcag | ccgggccttg tggagtgcgg | gtctctgctg | 60 |
| cggacgccgg | gggccggcgc | ggcgttggcc | gccccggcc tcgccgagtg | cagcgcgccc | 120 |
| gaaggccagt | gcctgcgctc | cgtccgcggc | ccggcgccca gggtgggcgg | ggaggccgcc | 180 |
| gcgcagtcgc | cgcacgctac | accgccggcg | ccgtcgtttc gcgtcgcccg | cttccggcca | 240 |
| ccgcggccgc | cattttgttc | gcgcggaagc | gccgcggtag ggtgggaacc | caagcgggag | 300 |
| agccgcggga | tttgcggccg | ccgccatgcc | gtcgtccccg ctgcgggtgg | cggtggtgtg | 360 |
| ctcgagcaac | cagaaccgga | gcatggaggc | gcacaacatc ctcagcaaac | ggggattcag | 420 |
| cgtccgatcc | tttggaacag | ggactcacgt | gaagcttcca ggaccagctc | ccgacaagcc | 480 |

```
caatgtttat gatttcaaaa ccacatatga ccagatgtac aatgatcttc ttaggaaaga      540
caaagaactc tatacacaga atgggatttt acatatgctg gacagaaata agagaatcaa      600
gccccggcca gaaagattcc agaactgcaa agacctgttt gatctgatcc tcacttgcga      660
agagagagtg tatgaccagg tggtggaaga tctgaattcc agagaacagg agacctgcca      720
gcctgtgcac gtggtcaatg tggacatcca ggacaaccac gaggaggcca ccctgggggc      780
gtttctcatc tgtgagctct gccagtgtat ccagcacacg gaagacatgg agaacgagat      840
cgacgagctg ctgcaggagt cgaggagaa gagtggccgc accttctgc acaccgtctg       900 cttctactga gcccagcgcc cgcatggagc cgcctctgga gcttcctgtt gttcatactt      960
tttccttcct gacatttgtt tttacttaca ggtgttctgc tggtgacggt agcattaccc     1020
aaataaactg tgcatatgaa atgggagagg agatgccaaa acgccagatg aaagcaatca     1080
agtttcttct tttccacttt tacttatgag caggatattg attacaaagt tttcttctt      1140 taaccaaaaa ggaaagacaa cggtttgtgt gcacttcccg acatacctgt gtcttcgtgt     1200
gcctgccttc cctccctcct ccccaccggg ccggactgta cagagccctg ctgcggcgtg     1260
ttaggaatga cctggaattg tcaataaaca gatgctgctg tcaaaaaaaa aaaaaaaa       1319

<210> SEQ ID NO 3
<211> LENGTH: 20
<212> TYPE: DNA
<213> ORGANISM: artificial sequence
<220> FEATURE:
<223> OTHER INFORMATION: a primer specific to IL-17 - sense primer

<400> SEQUENCE: 3
cctcaaagct cagcgtgtcc                                                    20

<210> SEQ ID NO 4
<211> LENGTH: 20
<212> TYPE: DNA
<213> ORGANISM: artificial sequence
<220> FEATURE:
<223> OTHER INFORMATION: a primer specific to IL-17 - antisense primer

<400> SEQUENCE: 4
gagctcactt ttgcgccaag                                                    20

<210> SEQ ID NO 5
<211> LENGTH: 23
<212> TYPE: DNA
<213> ORGANISM: artificial sequence
<220> FEATURE:
<223> OTHER INFORMATION: a primer specific to IL-21 - sense primer

<400> SEQUENCE: 5
cccttgtctg tctggtagtc atc                                                23

<210> SEQ ID NO 6
<211> LENGTH: 21
<212> TYPE: DNA
<213> ORGANISM: artificial sequence
<220> FEATURE:
<223> OTHER INFORMATION: a primer specific to IL-21 - antisense primer

<400> SEQUENCE: 6
atcacaggaa gggcatttag c                                                  21

<210> SEQ ID NO 7
<211> LENGTH: 22
```

```
<212> TYPE: DNA
<213> ORGANISM: artificial sequence
<220> FEATURE:
<223> OTHER INFORMATION: a primer specific to IL-1beta - sense primer

<400> SEQUENCE: 7
ggatgaggac atgagcacat tc                                              22

<210> SEQ ID NO 8
<211> LENGTH: 22
<212> TYPE: DNA
<213> ORGANISM: artificial sequence
<220> FEATURE:
<223> OTHER INFORMATION: a primer specific to IL-1beta - antisense
      primer

<400> SEQUENCE: 8
ggaagacagg cttgtgctct ga                                              22

<210> SEQ ID NO 9
<211> LENGTH: 22
<212> TYPE: DNA
<213> ORGANISM: artificial sequence
<220> FEATURE:
<223> OTHER INFORMATION: a primer specific to IL-6 - sense primer

<400> SEQUENCE: 9
aacgatgatg cacttgcaga aa                                              22

<210> SEQ ID NO 10
<211> LENGTH: 22
<212> TYPE: DNA
<213> ORGANISM: artificial sequence
<220> FEATURE:
<223> OTHER INFORMATION: a primer specific to IL-6 - antisense primer

<400> SEQUENCE: 10
tctgaaggac tctggctttg tc                                              22

<210> SEQ ID NO 11
<211> LENGTH: 20
<212> TYPE: DNA
<213> ORGANISM: artificial sequence
<220> FEATURE:
<223> OTHER INFORMATION: a primer specific to IL-6 receptor - sense
      primer

<400> SEQUENCE: 11
atttgtgtgc tgaaggaggc                                                 20

<210> SEQ ID NO 12
<211> LENGTH: 20
<212> TYPE: DNA
<213> ORGANISM: artificial sequence
<220> FEATURE:
<223> OTHER INFORMATION: a primer specific to IL-6 receptor- antisense
      primer

<400> SEQUENCE: 12
aaaggacagg atgttgcagg                                                 20

<210> SEQ ID NO 13
<211> LENGTH: 20
<212> TYPE: DNA
<213> ORGANISM: artificial sequence
<220> FEATURE:
<223> OTHER INFORMATION: a primer specific to IL-4 - sense primer
```

```
<400> SEQUENCE: 13
cgagtaatct tgcatgatgc                                                     20

<210> SEQ ID NO 14
<211> LENGTH: 21
<212> TYPE: DNA
<213> ORGANISM: artificial sequence
<220> FEATURE:
<223> OTHER INFORMATION: a primer specific to IL-4 - antisense primer

<400> SEQUENCE: 14
acggagatgg tgccaaacgt c                                                   21

<210> SEQ ID NO 15
<211> LENGTH: 20
<212> TYPE: DNA
<213> ORGANISM: artificial sequence
<220> FEATURE:
<223> OTHER INFORMATION: a primer specific to IL-10 - sense primer

<400> SEQUENCE: 15
ggcccagaaa tcaaggagca                                                     20

<210> SEQ ID NO 16
<211> LENGTH: 20
<212> TYPE: DNA
<213> ORGANISM: artificial sequence
<220> FEATURE:
<223> OTHER INFORMATION: a primer specific to IL-10 - antisense primer

<400> SEQUENCE: 16
agaaatcgat gacagcgcct                                                     20

<210> SEQ ID NO 17
<211> LENGTH: 144
<212> TYPE: DNA
<213> ORGANISM: artificial sequence
<220> FEATURE:
<223> OTHER INFORMATION: Polynucleotide sequence comprising three
      repeats of HA epitope tag

<400> SEQUENCE: 17
aagcttgcca ccatggaatt cttttaccca tacgatgttc ctgactatgc gggctatccc         60
tatgacgtcc cggactatgc aggatcctat cgatatgacg ttccagatta cgctggtctc       120
gagcatgcat ctagaggagg gccc                                              144
```

METHOD FOR INHIBITING STAT3 ACTIVITY COMPRISING ADMINISTERING SSU72

CROSS-REFERENCE TO RELATED APPLICATIONS

This application is a Continuation Application of U.S. application Ser. No. 15/563,435, filed Sep. 29, 2017, which is a National Stage of International Application No. PCT/KR2016/003352, filed Mar. 31, 2016, claiming priorities to Korean Patent Application No. 10-2015-0045114 filed Mar. 31, 2015, and Korean Patent Application No. 10-2016-0038934, filed Mar. 31, 2016, the disclosures of which are incorporated herein by reference in their respective entireties.

SEQUENCE LISTING

The content of the electronically submitted sequence listing, file name: Q260442_revised sequence listing.txt; size: 7,401 bytes; and date of creation: Nov. 9, 2022, filed herewith, is incorporated herein by reference in its entirety.

TECHNICAL FIELD

The present disclosure relates to a composition for preventing or treating an autoimmune disease, in which the composition includes Ssu72 as an active ingredient.

BACKGROUND ART

Immunization is one of the self-protection systems of a living body for all the external high-molecular substances (antigen) that are invaded or injected into living tissue. There is a major component of the immune system, lymphocytes, which are white blood cells that are made from bone marrow and circulate along the blood with lymphatic tissue or organ, mainly lymph node spleen tonsil. As a cell involved in the immune response, B cells rapidly proliferate when stimulated with the appropriate antigen and form a clone producing a specific antibody (immunoglobulin) to neutralize the antigen, and the antibodies that B cells generate circulate in the body fluid and perform humoral immunity. In addition, T cells are generated in the thymus and migrate to lymphatic tissue, which are responsible for cell-mediated immunity that directly attacks antigen.

On the other hand, one of the most important characteristics of all normal individuals is that they do not react harmful to the antigenic substances constituting the self, but have the ability to recognize, react, and eliminate many non-self-antigens. As such, the non-response of a living body to a self-antigen is referred to as immunologic unresponsiveness or tolerance.

If problems arise in inducing or maintaining such self-tolerance, an immune response to the self-antigen occurs, thereby attacking self-tissues, so that autoimmune diseases such as multiple sclerosis, type 1 diabetes, rheumatoid arthritis, and Hashimoto's thyroiditis are caused. Moreover, immunorejection response occurs after the surgical procedure such as transplantation.

Specifically, an autoimmune disease is a disease caused by an adverse reaction to a self-cell. Currently, as a therapeutic agent, immunosuppressants that block signal transduction pathways in T cells are most commonly used. However, there is a problem in that these immunosuppressants have side effects such as toxicity, infection, lymphoma, diabetes, tremor, headache, diarrhea, hypertension, nausea, and renal dysfunction. Accordingly, it is necessary to develop a new therapeutic agent which has no side effects and is inexpensive and has an excellent therapeutic effect.

DISCLOSURE

Technical Problem

In this regard, an object of the present disclosure is to provide a pharmaceutical composition for preventing or treating an immune disease, in which the pharmaceutical composition includes an Ssu72 protein or a polynucleotide encoding an Ssu72 protein.

In addition, another object of the present invention is to provide a method for screening a therapeutic agent for diseases associated with activation of STAT3.

Technical Solution

In order to achieve the object of the present disclosure as described above, the present disclosure provides a pharmaceutical composition for preventing or treating an immune disease, in which the pharmaceutical composition includes an Ssu72 protein or a polynucleotide encoding an Ssu72 protein.

In one embodiment of the present invention, the Ssu72 protein may be one consisting of the amino acid sequence of SEQ ID NO: 1.

In one embodiment of the present invention, the polynucleotide encoding the Ssu72 protein may be one consisting of the base sequence of SEQ ID NO: 2.

In one embodiment of the present invention, the polynucleotide may be included in an expression vector.

In one embodiment of this invention, the immune disease may be selected from the group consisting of rheumatoid arthritis, osteoporosis, plasmacytosis, hyperimmunoglobulinemia, anemia, nephritis, cachexia, stock-farmer's disease, vascular proliferative nephritis, multiple sclerosis, uveitis, chronic thyroiditis, delayed hypersensitivity, contact dermatitis, atopic dermatitis, systemic erythematosus, Crohn's disease, pancreatitis, psoriasis, dry eye syndrome, Sjögren's syndrome, multiple sclerosis, juvenile idiopathic atrophy, diabetes, and Alzheimer's, which are the diseases associated with activation of STAT3.

In addition, the present disclosure provides a method for screening a therapeutic agent for a disease associated with activation of STAT3, in which the method includes treating a candidate substance in a cell or tissue including an Ssu72 gene or an Ssu72 protein, and measuring the amount of expression of Ssu72 gene or the amount of Ssu72 protein or the activity of Ssu72 protein.

In one embodiment of the present invention, when the amount of expression of Ssu72 gene or the amount of Ssu72 protein or the activity of Ssu72 protein is increased as compared with a control group that is not treated with a candidate substance, the method may further include determining the candidate substance as a substance for preventing or treating a disease associated with the activation of STAT3.

In one embodiment of the present invention, the amount of expression of Ssu72 gene or the amount of Ssu72 protein or the activity of Ssu72 protein may be performed by any one of the methods selected from the group consisting of reverse transcription polymerase chain reaction (RT-PCR), real-time reverse transcription polymerase chain reaction, coimmunoprecipitation, enzyme-linked immunosorbentassay, radioimmunoassay (RIA), immunohistochemistry, western blotting, and flow cytometry (FACS).

In one embodiment of the present invention, the diseases associated with activation of STAT3 may be selected from the group consisting of rheumatoid arthritis, osteoporosis, plasmacytosis, hyperimmunoglobulinemia, anemia, nephritis, cachexia, stock-farmer's disease, vascular proliferative nephritis, multiple sclerosis, uveitis, chronic thyroiditis, delayed hypersensitivity, contact dermatitis, atopic dermatitis, systemic lupus erythematosus, Crohn's disease, pancreatitis, psoriasis, dry eye syndrome, Sjögren's syndrome, multiple sclerosis, juvenile idiopathic atrophy, diabetes, and Alzheimer's.

Advantageous Effects

Ssu72 according to the present disclosure has an effect of effectively inhibiting the activity of STAT3, and thus can inhibit the expression of inflammatory cytokines when Ssu72 is overexpressed, while at the same time, the expression of IL-4 and IL-10, which are factors associated with immunoregulatory T cells, can be promoted and ultimately prevent and treat immune diseases, preferably STAT3 mediated diseases.

MODES OF THE INVENTION

Figure 1:
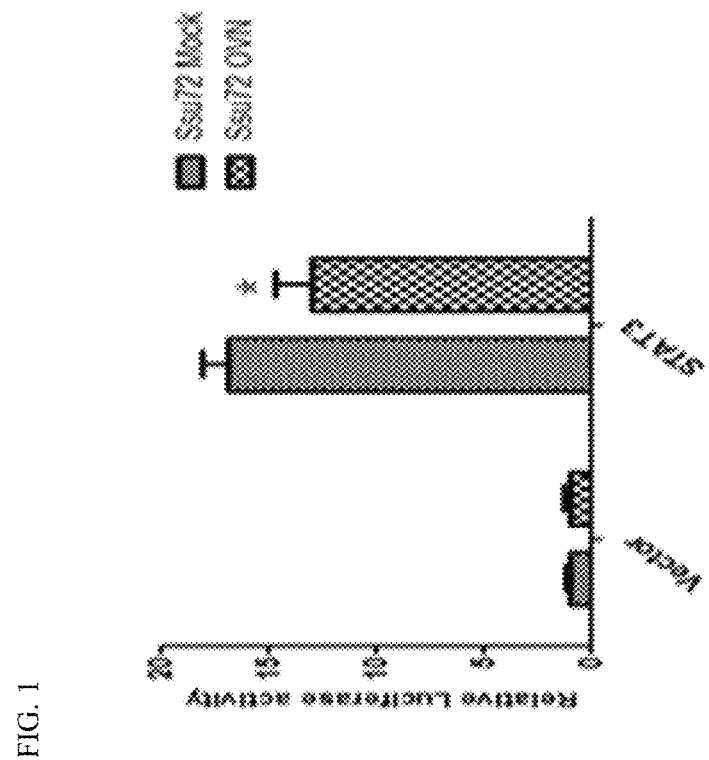
FIG. 1 illustrates the results of confirming the inhibitory activity of STAT3 phosphorylation in accordance with the over-expression of Ssu72 by western blotting.
Figure 1:
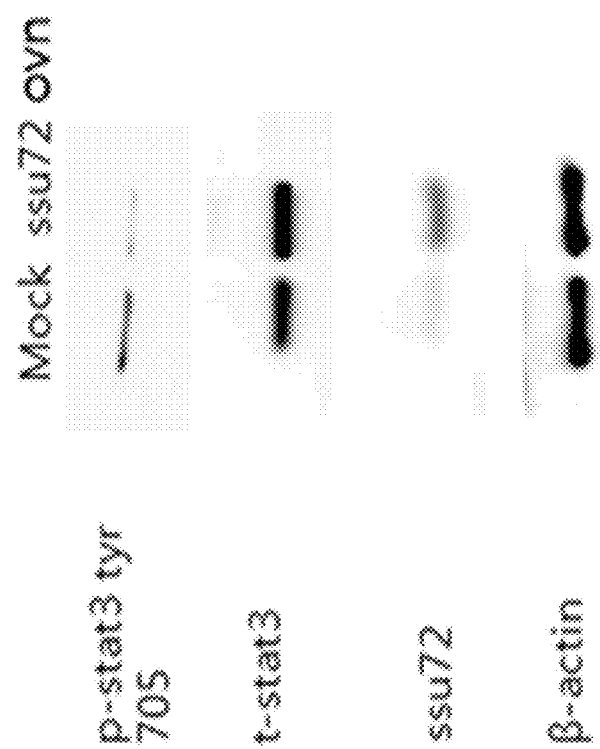

The present disclosure is characterized in that Ssu72 can effectively inhibit the activity of STAT3 and thus can be used as a therapeutic agent for immune diseases.

STATs are known as transcription factors that are activated by phosphorylation by Januse kinase (JAK), a type of receptor tyrosine kinase, epidermal growth factor receptor (EGFR), platelet-derived growth factor receptor (PDGFR), and the like (Darnell J E Jr. Science. 277, 1630-1635 (1997)). It is known that STATs activated by phosphorylation induce transcription of various genes associated with the disease by forming a dimer, migrating into the nucleus and binding in the vicinity of a promoter of a target gene (Darnell J E Jr. Science. 277, 1630-1635 (1997); Bromberg J F, et al., Cell. 98, 295-303 (1999)). One of the STATs protein classes, STAT3, is known to be overactivated in various types of human tumors including blood cancer and solid tumors (Bromberg J F, et al., Cell. 98, 295-303 (1999)). The overactivated STAT3 is known to promote tumorogenesis of mutated cells by promoting the expression of target genes such as Bcl-XL, c-myc, and cyclin D1 associated with survival, proliferation and growth of cancer cells (Vera J, et al., Prog Biophys Mol Biol. 106, 426-434 (2011); Turkson J. Expert Opin Ther Targets. 8, 409-422 (2004)). In addition, recent reports suggest a possibility that STAT3 inhibitors would be used as potential anticancer agents (Duan H, et al., Oncogene., 27, 6720-6728 (2008); Bai L, et al., Int J Cancer 130, 2693-2702 (2012); Kan C E, et al., Cancer Res. 71, 6930-6939 (2011)).

In addition, it is known that signal transducers and activators of transcription 3 (STAT3) plays a role as another important transcription factor in addition to NF-B in autoimmune diseases or osteoporosis including rheumatoid arthritis. In particular, STAT3 is well known to be activated by the cytokine IL-6 and is also known to be activated by epidermal growth factor (EGF). Recently, many studies on the relationship between osteoporosis and IL-6 have been reported. In particular, it has been verified through animal models that STAT3 activity induced by IL-6 plays an important role in osteoclast differentiation and bone formation. (Bone 2006, 39, 505-512). In STAT3-deficient mice, bone mineral density and bone volume were reduced, and there was an increase in the number of osteoclasts that negatively affected osteoporosis (BBRC 2005, 328, 800-807).

As such, the activation of STAT3 is related to the pathogenesis of autoimmune diseases including rheumatoid arthritis, and thus when it is inhibited, STAT3 mediated diseases can be treated.

In addition, the immune system in the body controls the specific immune response to the autoantigen in the normal state and inhibits the immune response to the external antigen. Examples are a pregnant woman's response to a fetus and an immune response to a microorganism in a chronic infection state. These phenomena are known to be induced by clonal deletion, clonal anergy, and active control by immunoregulatory T cells (Treg) as a mechanism by which antigen-specific immune tolerance can be induced. On investigation of some of the patients who have obtained immune tolerance to the transplantation antigen by chance or animal models which have experimentally induced immune tolerance, it was confirmed that all three mechanisms are involved in transplantation immune tolerance. In particular, recently, immunoregulatory T lymphocytes have been regarded as important cells that regulate almost all immune responses of a living body such as autoimmunity, tumor immunity, and infectious immune response as well as transplantation immune response.

In particular, immunoregulatory T cells, i.e., immunoregulatory T lymphocytes (Tregs), whose existence has been revealed recently, can be broadly divided into natural Treg and adaptive Treg cells. CD4+CD25+ T cells, which are natural Tregs, are given immunosuppressive functions from the time when the cells are newly generated in the thymus, and are present in a frequency of 5 to 10% of the peripheral CD4+ T lymphocytes of normal individuals. Although the immunosuppressive mechanism of this cell has not yet been elucidated yet, it has been recently revealed that the gene expression regulator of Foxp3 plays an important role in the differentiation and activity of this cell. In addition, peripheral natural T cells can be differentiated into cells exhibiting an immunosuppressive effect upon being stimulated by a self or external antigen under a specific environment, which is referred to as an adaptive or inducible Treg, and includes Tr1 that secretes IL-10, Th3 that secretes TGF-, CD8 Ts, and the like.

In addition, these T cells are also differentiated into Th17 cells through a differentiation process in addition to Treg cells. Th17 cells are common to Treg cells in the presence of TGF-$\beta$, whereas Treg cells do not require IL-6. In the case of Th17 cells, it is differentiated in the presence of IL-6 together with TGF-$\beta$ and secretes IL-17.

Th17 cells, however, have cytotoxic properties that maximize the signal of the inflammatory response and accelerate disease progression. Accordingly, differentiation into Th17 cells or inhibition of the activity is one of the methods for treating immune diseases.

In this regard, Ssu72 of the present disclosure inhibits the activity of Th17 cells and at the same time, promotes the activity of Treg cells. Therefore, it is possible to treat immune diseases more effectively than the conventionally developed therapeutic agents for immune diseases.

On the other hand, Ssu72 is known as a molecule involved in transcription with RNA polymerase II CTD phosphatase. However, little is known about the function and role of Ssu72 in vivo.

However, the present disclosure shows that STAT3 activity can be effectively inhibited, specifically STAT3 phosphorylation, and inhibit the production of inflammatory cytokines. At the same time, the present disclosure is characterized in that it is eventually possible to effectively prevent and treat STAT3 mediated diseases by promoting the activity of promoting the production of immunoregulatory T cell-related cytokines.

Accordingly, the present disclosure can provide a pharmaceutical composition for preventing or treating immune diseases including Ssu72 protein or a polynucleotide encoding Ssu72 protein.

Preferably, the Ssu72 protein may have the amino acid sequence of SEQ ID NO: 1, and the polynucleotide encoding the Ssu72 protein may have the base sequence of SEQ ID NO: 2.

In addition, the Ssu72 protein according to the present disclosure may preferably be a functional equivalent to a polypeptide having the amino acid sequence of SEQ ID NO: 1. The "functional equivalent" means a polypeptide having at least 60%, preferably 70%, more preferably 80% or more sequence homology with the amino acid sequence of SEQ ID NO: 2 as a result of amino acid addition, substitution or deletion, and exhibiting substantially homogenous activity as Ssu72 of the present invention. Herein, "substantially homogenous activity" means the activity of Ssu72 described above. Such functional equivalents may include, for example, amino acid sequence variants in which some of the amino acids of the Ssu72 amino acid sequence according to the present invention are substituted, deleted or added. Substitution of amino acids can be preferably conservative substitutions, and examples of conservative substitutions of amino acids present in nature are provided as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn), and sulfur-containing amino acids (Cys, Met). Deletion of the amino acid may preferably be located at a site that is not directly involved in the activity of Ssu72 of the present invention. In addition, the range of the functional equivalents may also include polypeptide derivatives in which some of the chemical structures of the polypeptides are modified while maintaining the basic skeleton of Ssu72 and its physiological activity. Examples are fusion proteins prepared by fusion with other proteins while maintaining structural changes to change stability, hypotonicity, volatility or solubility of the polypeptide of the present disclosure and physiological activity.

In addition, the polynucleotide encoding the ssu72 protein may be introduced into an expression vector such as a plasmid or a viral vector by a known method and then the expression vector may be introduced into the target cell in an expression form by transduction or transfection by various methods known pertinent in the art.

A plasmid expression vector is a method for directly delivering plasmid DNA to human cells using an approved FDA-approved gene transfer method that can be used in humans (Nabel, E. G. et al., *Science*, 249:1285-1288, 1990), and has an advantage in that plasmid DNA can be homogeneously purified, unlike the viral vector. As a plasmid expression vector that can be used in the present invention, mammalian expression plasmids known in the pertinent art may be used. In one embodiment of the present invention, HA vector (pHA) was used to prepare a recombinant expression vector, an HA-Ssu72 vector, into which an Ssu72 gene was inserted.

A plasmid expression vector including a nucleic acid according to the present disclosure may be introduced into the target cell by a method known in the pertinent art, for example, but not limited thereto, transient transfection, microinjection, transduction, cell fusion, calcium phosphate precipitation, liposome-mediated transfection, DEAE-dextran-mediated transfection, polybrene-mediated transfection, electroporation, gene gun, and other known methods for introducing DNA into cells (Wu. et al., J. Bio. Chem., 267:963-967, 1992; Wu. et al., Bio. Chem., 263:14621-14624, 1988).

In addition, the vector capable of expressing Ssu72 may be administered into cells, tissues or the body by a known method, for example, topically, parenterally, orally, nasally, intravenously, intramuscularly, subcutaneously, or may be administered by any other suitable means. In particular, the vector may be injected directly into an amount effective to treat the target tissue or target cell.

Further, the present disclosure can provide a method for screening a therapeutic agent for a disease associated with activation of STAT3 using Ssu72.

That is, the method for screening a therapeutic agent for a disease associated with activation of STAT3 according to the present disclosure includes treating a candidate substance to a cell or tissue including the Ssu72 gene or the Ssu72 protein and measuring the expression degree of the Ssu72 gene or the amount of the Ssu72 protein or the activity of the Ssu7272 protein.

The method according to the present disclosure is a method for discovering a therapeutic agent for a disease associated with the activation of a new STAT3 using Ssu72, in which the term "candidate substance" refers to an unknown substance used in screening to check whether it affects the amount of expression of the Ssu72 gene, the amount of the Ssu72 protein or the activity of the Ssu72 protein. The sample may include compounds, proteins, peptides, oligonucleotides, or natural extracts, but is not limited thereto.

The treatment of the candidate substance can be performed in a process of culturing the same preferably after treating the candidate substance in a cell or tissue including the Ssu72 gene or the Ssu72 protein.

In addition, the intracellular level increase of the Ssu72 protein means that the expression of the Ssu72 gene is increased or the degradation of the Ssu72 protein is inhibited, thereby increasing the amount of the Ssu72 protein. The Ssu72 gene expression includes a process of transcription of the Ssu72 gene and translation into a protein. Accordingly, when the candidate substance increases the expression of the Ssu72 gene and the level of the protein in the cell, the candidate substance can be regarded as a new therapeutic agent capable of treating a disease associated with the activation of STAT3.

The measurement of the expression level of the gene is preferably configured to measure the level of mRNA, and a method for measuring mRNA levels includes reverse transcription polymerase chain reaction (RT-PCR), real-time reverse transcription polymerase chain reaction, RNase protection assay, northern blot, DNA chip, and the like, but is not limited thereto.

In addition, an amount of the protein or the activity of the protein can be measured by using an antibody. In this case, the marker protein in a biological sample and the antibody specific thereto form a conjugate, that is, an antigen-antibody complex. In addition, an amount of formation of an antigen-antibody complex can be quantitatively measured through the magnitude of the signal of a detection label. Such detection labels may be selected from the group consisting of enzymes, fluorescent substances, ligands, luminous substances, microparticles, redox molecules, and radioisotopes, but is not limited thereto. Analytical methods for measuring protein levels include, but are not limited to, western blot, ELISA, radioimmunoassay, radioimmunodiffusion, ouchterlony immunodiffusion, rocket immunoelectrophoresis, tissue immuno staining, immunoprecipitation assay, complement fixation assay, FACS, and protein chip, etc.

As described above, various methods known in the pertinent art may be used to measure the expression amount of the Ssu72 gene, the amount of the Ssu72 protein, or the activity of the Ssu72 protein. Preferably, the reverse transcription polymerase chain reaction (RT-PCR), real-time reverse transcription polymerase chain reaction, coimmunoprecipitation, enzyme-linked immunosorbentassay, radioimmunoassay (RIA), immunohistochemistry, western blotting and flow cytometry (FACS) may be used.

In addition, the composition according to the present disclosure can be used as a pharmaceutical composition capable of preventing and treating diseases associated with immune diseases, preferably the activation of STAT3, and the pharmaceutical composition may further include a pharmaceutically acceptable carrier. The term "pharmaceutically acceptable" as used herein refers to a composition that is physiologically acceptable and does not normally cause an allergic reaction such as gastrointestinal disorder, dizziness, or the like when administered to humans, or its similar reactions. Pharmaceutically acceptable carriers include carriers for oral administration such as, for example, lactose, starch, cellulose derivatives, magnesium stearate, stearic acid, etc., and carriers for parenteral administration such as water, suitable oils, saline solution, aqueous glucose, glycol, etc., and may additionally include stabilizers and preservatives. Suitable stabilizers include antioxidants such as sodium hydrogen sulfite, sodium sulfite, or ascorbic acid. Suitable preservatives include benzalkonium chloride, methyl- or propyl-paraben, and chlorobutanol. Other pharmaceutically acceptable carriers may be those listed in the following documents (Remington's Pharmaceutical Sciences, 19th ed., Mack Publishing Company, Easton, Pa., 1995). The pharmaceutical composition according to the present disclosure may be formulated into a suitable form according to a method known in the pertinent art, together with a pharmaceutically acceptable carrier as described above. That is, the pharmaceutical composition of the present disclosure may be prepared in various parenteral or oral administration forms according to known methods, and representative examples of parenteral administration formulations include isotonic aqueous solutions or suspensions which are preferably used as injectable formulations. The injectable formulations may be prepared according to the techniques known in the pertinent art using suitable dispersing agents or wetting agents and suspending agents. For example, each ingredient may be formulated for injection by being dissolved in a saline solution or a buffer solution. Formulations for oral administration also include, but are not limited to, powders, granules, tablets, pills, and capsules, etc.

The pharmaceutical composition formulated as described above may be administered in an effective amount through various routes including oral, transdermal, subcutaneous, intravenous, or muscular. The term "effective amount" as used herein refers to an amount that shows a preventive or therapeutic effect when administered to a patient. The dosage of the pharmaceutical composition according to the present disclosure can be appropriately selected depending on the route of administration, subject for administration, age, gender, weight, individual difference, and disease state. Preferably, the pharmaceutical composition of the present disclosure may vary in the content of an active ingredient depending on the degree of diseases, but may be repeatedly administered several times a day, preferably at an effective dose of 1~10000 µg/weight kg/day, more preferably 10~1000 mg/weight kg/day. In addition, the composition of the present disclosure may be administered in combination with a known compound having an effect of preventing, ameliorating or treating an immune disease.

In addition, immune diseases that can be treated and prevented by the composition including Ssu72 of the present disclosure may include, but are not limited to, rheumatoid arthritis, osteoporosis, plasmacytosis, hyperimmunoglobulinemia, anemia, nephritis, cachexia, stock-farmer's disease, vascular proliferative nephritis, multiple sclerosis, uveitis, chronic thyroiditis, delayed hypersensitivity, contact dermatitis, atopic dermatitis, systemic erythematosus, Crohn's disease, pancreatitis, psoriasis, juvenile idiopathic atrophy, diabetes, and Alzheimer's.

In the present invention, the STAT3 mediated disease refers to a disease caused by activation of the STAT3 pathway. It is known in the pertinent art that overexpression, hypersecretion, or hyperactivity of interleukin-1β and/or interleukin-6 induces activation of the STAT3 pathway. Furthermore, interleukin-1β and/or interleukin-6 is known to increase expression, secretion or activity by inflammatory diseases, autoimmune diseases, destructive bone diseases, infectious diseases, degenerative diseases, and necrotic diseases, etc. These diseases are known to be due to STAT3 pathway activation induced by interleukin-1β and/or interleukin-6. Accordingly, in the development of therapeutic agents for the above diseases, various methods such as the development of an anti-interleukin receptor capable of inhibiting interleukin-1β and/or interleukin-6 inducing STAT3 pathway activation or development of an inhibitor capable of directly inhibiting STAT3 have been studied, and the present disclosure provides the use of Ssu72 as a novel inhibitor capable of inhibiting STAT3.

Hereinafter, the present disclosure will be described in more detail by way of examples. It will be apparent to a person having ordinary skill in the pertinent art that these embodiments are for illustrative purposes only and that the scope of the present disclosure is not construed as being limited by these examples.

Example 1

Preparation of Recombinant Vector into which Ssu72 was Introduced

Figure 7:
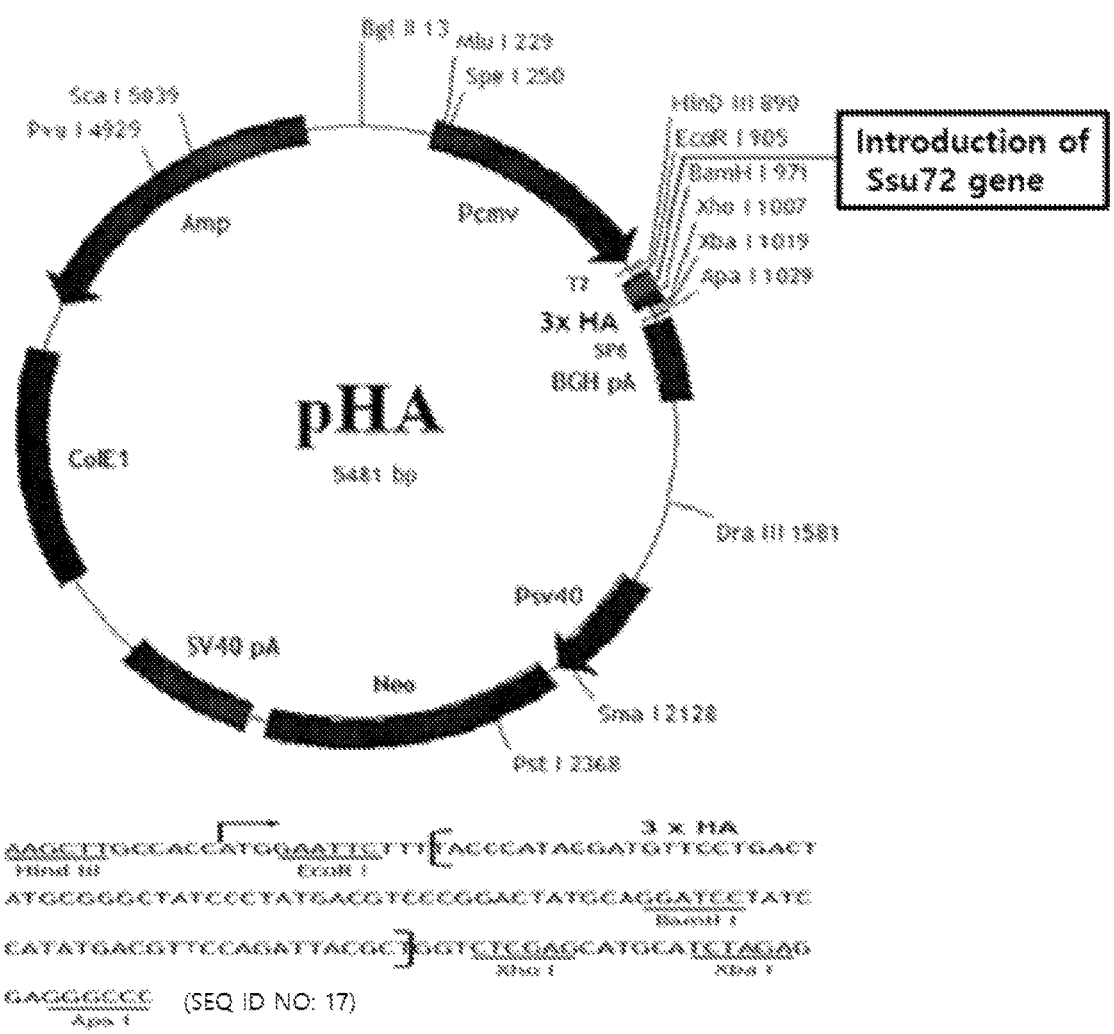
FIG. 7 illustrates an Ssu72 overexpressing recombinant vector map according to one embodiment of the present invention.

A recombinant vector for overexpressing Ssu72 was prepared. To do this, a Ssu72 gene was inserted under the promoter of CMV IE (human cytomegalovirus immediate early promoter), and a cloning was performed. The recombinant vector pHA-Ssu72 was prepared from the cassette listing the SV40 polyadenylation signal sequence, and the vector map of the recombinant vector is illustrated in FIG. 7.

Example 2

STAT3 Activity Inhibitory Effect Analysis by Overexpression of Ssu72

<2-1> Western Blot

In order to confirm whether Ssu72 overexpression could inhibit the activity of STAT3, the recombinant expression vector prepared in Example 1 was transduced into NIH/3T3 cells, and IL-6 was treated in the cells at a concentration of 20 ng/ml for 1 hour. After inducing the inflammatory environment, the degree of phosphorylation of STAT3 was confirmed by western blot upon overexpression of Ssu72. western blotting was used to obtain a cell lysate of IL-6 treated cells overexpressing Ssu72 to obtain a protein fraction, followed by p-STAT3 tyr 705 (mouse, cell signaling), total STAT3 (mouse, cell signaling), Ssu72 (mouse, cell signaling), and beta-actin (mouse, santacruz) antibodies, respectively.

<2-2> Luciferase Assay

In order to confirm whether Ssu72 overexpression could inhibit the activity of STAT3, the recombinant expression vector prepared in Example 1 was transduced into NIH/3T3 cells, and IL-6 was treated in the cells at a concentration of 20 ng/ml for 1 hour. After inducing the inflammatory environment, the degree of activation of STAT3 was confirmed by luciferase assay upon overexpression of Ssu72. luciferase assay was used to obtain a cell lysate of IL-6 treated cells overexpressing Ssu72 to obtain a protein fraction, followed by the use of luciferase and STOP & Glu solution capable of measuring Renilla and STAT3.

As a result of the analysis, as illustrated in FIG. 1, when Ssu72 was overexpressed in the inflammation-induced state, the activation of STAT3 has been shown to be significantly decreased. Accordingly, through these results, Ssu72 was shown to effectively inhibit STAT3 activity in the inflammatory environment.

<2-3> Confocal Microscopy Analysis

Confocal microscopy analysis was carried out for the same cell population used in Example <2-1>. To do this, the cell samples stored at −70° C. after the cryo section was first taken out to be dried in a hood for 1 hour. Then, the cells were fixed with cold acetone undiluted solution for 15 minutes, and then a coplin jar was used. After taking out the slide contained in the coplin jar and wiping the back side, it was dried in the hood for 2 minutes, washed 3 times with 1×PBS buffer for tissue for 5 minutes, blocked with 10% normal goat serum for 30 minutes at room temperature. 100 μl of the 1st Ab was added per tissue, followed by reaction at room temperature for 1 hour and then overnight at 4° C. The next day, after the sample was taken out and the slide was inserted into the staining jar, it was washed with 1×PBS for 15 minutes, the moisture around each block of the slide was carefully wiped off. 100 μl of the secondary antibody was added again to the slide, and then was reacted for 2 hours at room temperature. It was washed three times for 5 minutes with 1×PBS buffer for tissue. When nuclear staining was needed, DAPI (−20° C. storage) was diluted at 1:500 and 100 μl per tissue was stained. After washing it with 1×PBS buffer for tissue 3 times for 5 minutes, the cells were sealed with fluorescent mounting medium and observed with a microscope.

Figure 2:
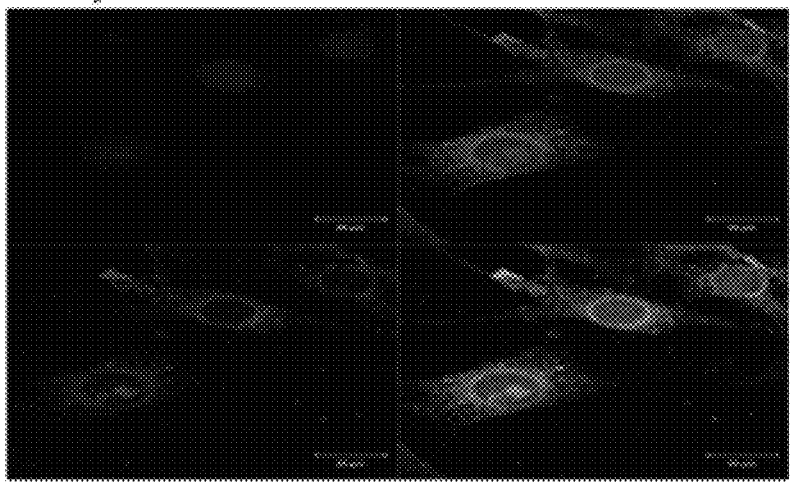
FIG. 2 illustrates the results of confirming the expression inhibitory effect of p-STAT3 in accordance with the overexpression of Ssu72 by confocal microscopy observation.
Figure 2:
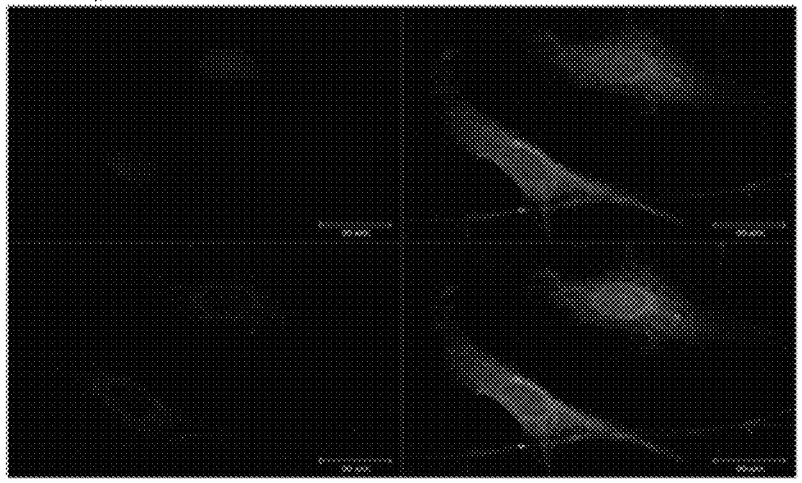

As a result of the analysis, as illustrated in FIG. 2, phosphorylation of STAT3 was decreased when Ssu72 was overexpressed in the same inflammatory state as the western blot result.

<2-4> Analysis of Inhibitory Effect of Ssu72 on Inflammatory Cytokine Expression Th17 Cytokine Inhibitory Effect In order to confirm whether Ssu72 inhibits the expression of inflammatory cytokines, NIH/3T3 cells were transduced into a recombinant expression vector in which Ssu72 is overexpressed, and the cells were stimulated with IL-6 at a concentration of 20 ng/ml for 1 hour. After that, DNA was obtained by a DNA Prep method known in the pertinent art. Then, RT-PCR was performed using a primer specific to IL-17 (sense primer: CCT CAA AGC TCA GCG TGT CC (SEQ ID NO:3), antisense primer: GAG CTC ACT TTT GCG CCA AG (SEQ ID NO:4)), and IL-21 (sense primer: CCC TTG TCT GTC TGG TAG TCA TC (SEQ ID NO:5), antisense primer: ATC ACA GGA AGG GCA TTT AGC (SEQ ID NO:6)).

Figure 3:
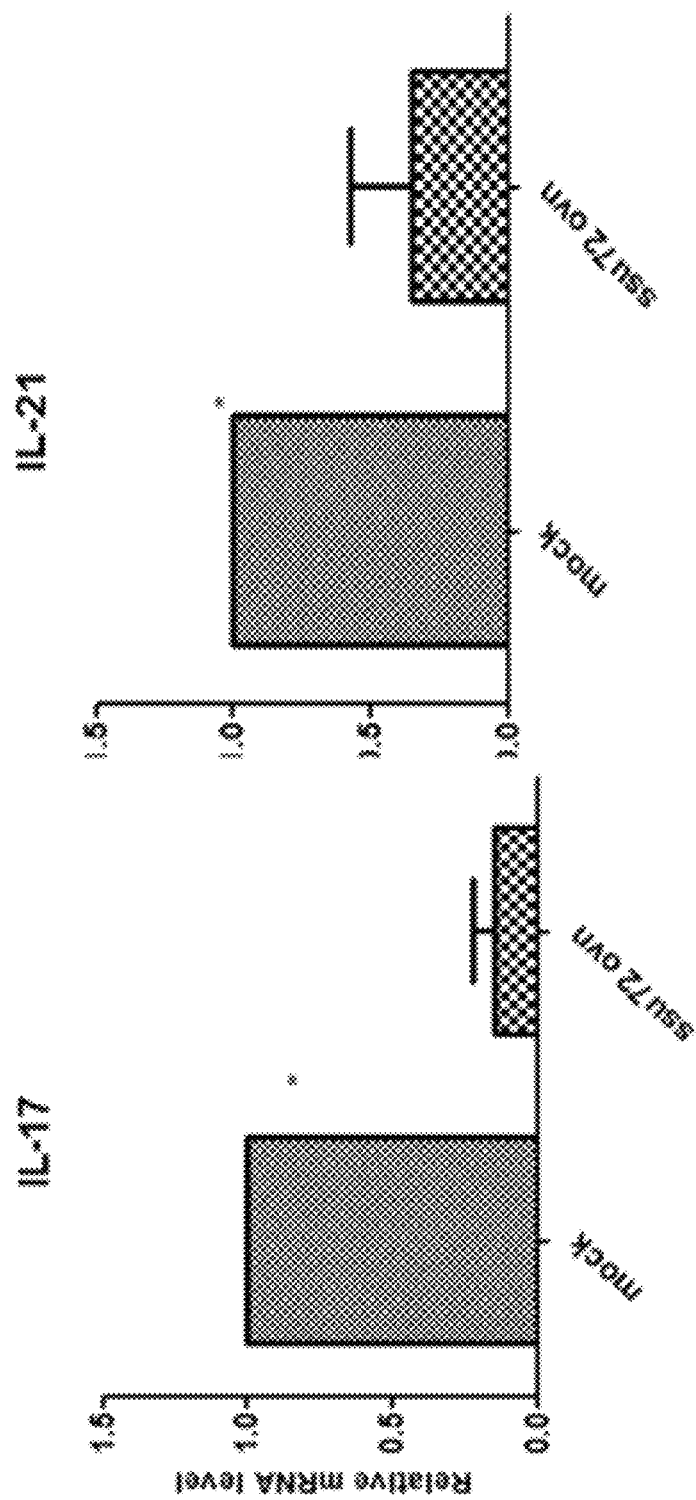
FIG. 3 illustrates the results of confirming the degree of expression inhibition of inflammatory cytokines IL-17 and IL-21 by Ssu72 through RT-PCR.

As a result of the analysis, as illustrated in FIG. 3, when Th17 cytokine (inflammatory cytokine), IL-17, was overexpressed, the expression amount was decreased by about 5-fold as compared with the control group that was not overexpressed, and the expression amount of IL-21 was decreased by about 3-fold.

Pro-Inflammatory Cytokine-Inhibitory Effect

In order to confirm whether Ssu72 has an activity of inhibiting the expression of pro-inflammatory cytokines, the present inventors obtained DNAs under the same experimental conditions as in the above <2-1>. Each primer, i.e., IL-1beta (sense primer: GGA TGA GGA CAT GAG CAC ATT C (SEQ ID NO:7), antisense primer: GGA AGA CAG GCT TGT GCT CTG A (SEQ ID NO:8)), IL-6 (sense primer: AAC GAT GAT GCA CTT GCA GAA A (SEQ ID NO:9), antisense primer: TCT GAA GGA CTC TGG CTT TGT C (SEQ ID NO:10), and IL-6 receptor (sense primer: ATT TGT GTG CTG AAG GAG GC (SEQ ID NO:11), antisense primer: AAA GGA CAG GAT GTT GCA GG (SEQ ID NO:12)) was used to confirm the expression degree of RNA of each gene by performing RT-PCR.

Figure 4:
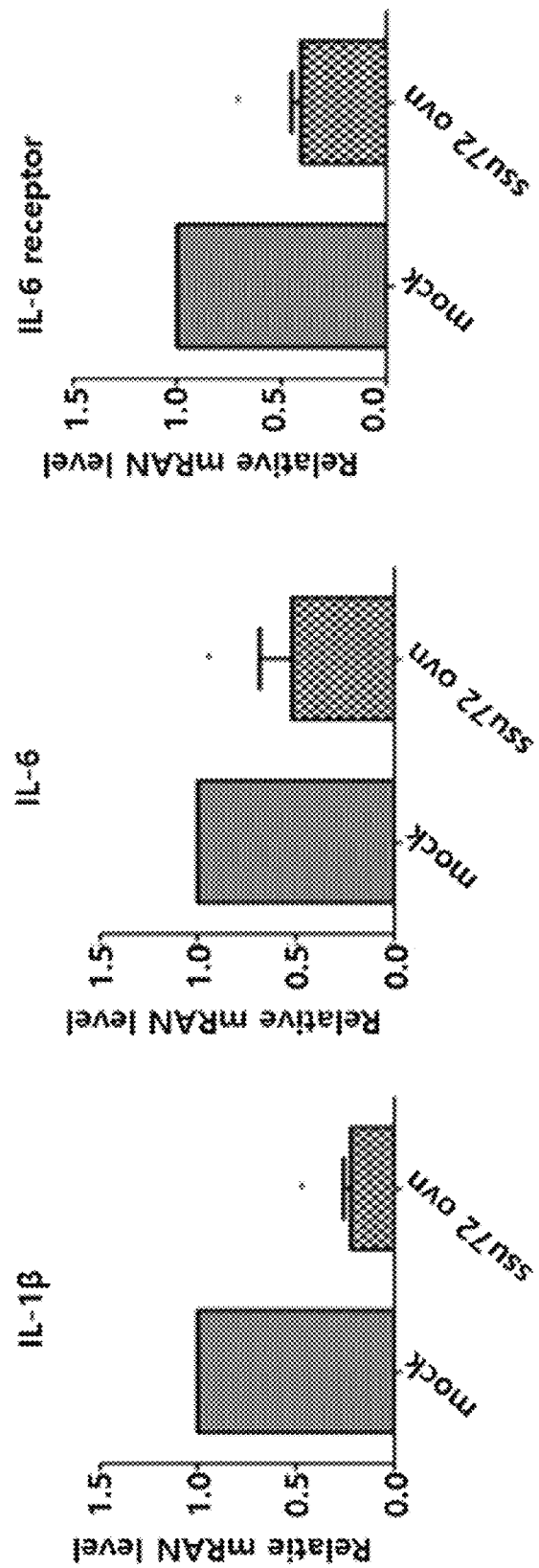
FIG. 4 illustrates the results of confirming the degree of expression inhibition of Th17 cytokines IL-1beta, IL-6, and IL-6 receptor by Ssu72 through RT-PCR.

As a result of the analysis, as illustrated in FIG. 4, when Ssu72 was overexpressed, the expression of IL-1beta was inhibited by about 4-fold and the expression of IL-6 and IL-6 receptors were inhibited by about 2fold, respectively, as compared with the control group that was not overexpressed.

Example 3

Analysis of Synergistic Effect of Th2-Related Cytokine of Ssu72

The following experiment was conducted to confirm whether Ssu72 synergizes the effects of the expression of Th2 and Treg-related cytokines. After DNA was obtained from each experimental group cell in the same manner as in the above Example 2, RT-PCR was performed using primers for IL-4 and IL-10, which are Th2 and Treg-related cytokines, that is, IL-4 (sense primer: CGA GTA ATC TTG CAT GAT GC (SEQ ID NO:13); antisense primer: ACG GAG ATG GTG CCA AAC GTC (SEQ ID NO:14)) and IL-10 (sense primer: GGC CCA GAA ATC AAG GAG CA (SEQ ID NO:15); antisense primer: AGA AAT CGA TGA CAG CGC CT (SEQ ID NO:16)).

Figure 5:
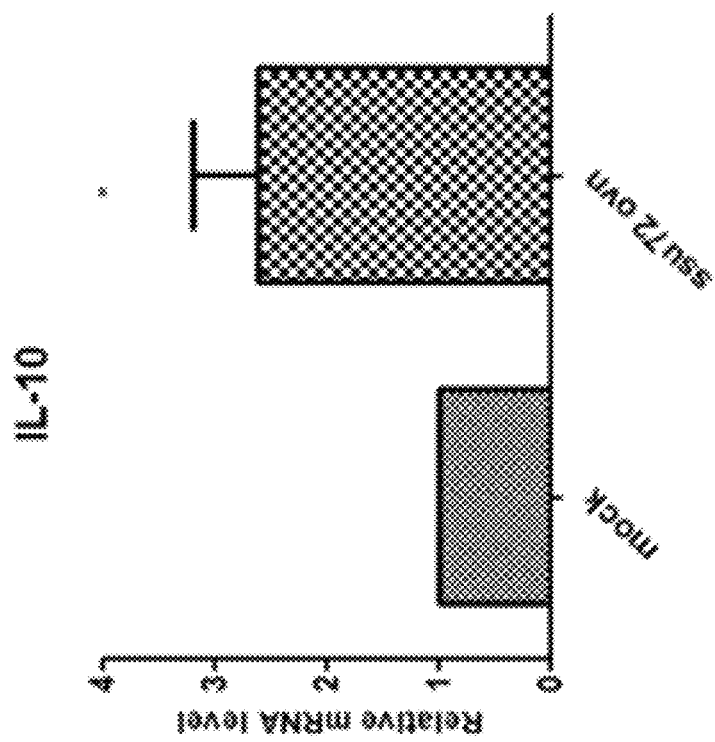
FIG. 5 illustrates the results of confirming the expression increase effect of Th2 and Treg-related cytokines IL-4 and IL-10 by Ssu72 through RT-PCR
Figure 5:
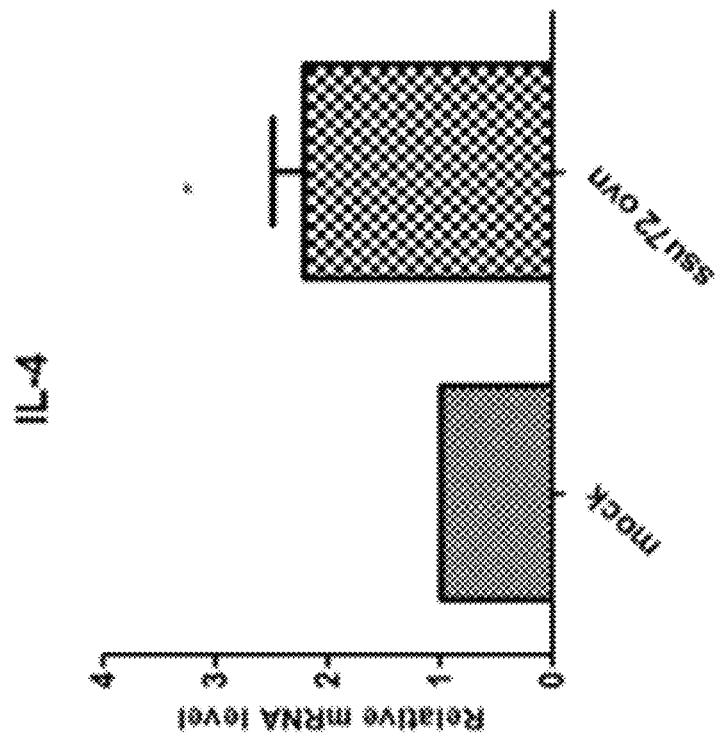

As a result of the analysis, as illustrated in FIG. 5, when Ssu72 was overexpressed, IL-4 was increased about 2.2-fold and IL-10 was increased about 2.7-fold as compared with the control group that was not overexpressed, indicating that Ssu72 played a role in increasing Th2 and Treg-related cytokine expression.

Example 4

Analysis of Treatment Effect of Ssu72 on Rheumatoid Arthritis

A mouse model in which rheumatoid arthritis was induced was prepared. DBA1/J mice were subcutaneously injected with type 2 collagen (intra-dermal) to induce arthritis. After induction of arthritis, an Ssu72 overexpression vector and a control group vector were injected into mice at a dose of 50 μl/mouse by hydrodynamic injection method once a week for 8 times in total. The hydrodynamic injection method is a method of injecting the recombinant vector of the present disclosure diluted in physiological saline into the tail vein by introducing the gene passing through a cell membrane into the cytoplasm using physical force. Type 2 collagen was mixed and injected into the tail with 1:1 volume ratio of adjuvant (IFA) for induction of a disease (booster). Two days later, the overexpression vector was injected into the right thigh. One week later, the overexpression vector was injected again into the left thigh. At this time, as a control group, mock vector not including Ssu72 gene was used. The symptoms of arthritis were then measured.

Figure 6:
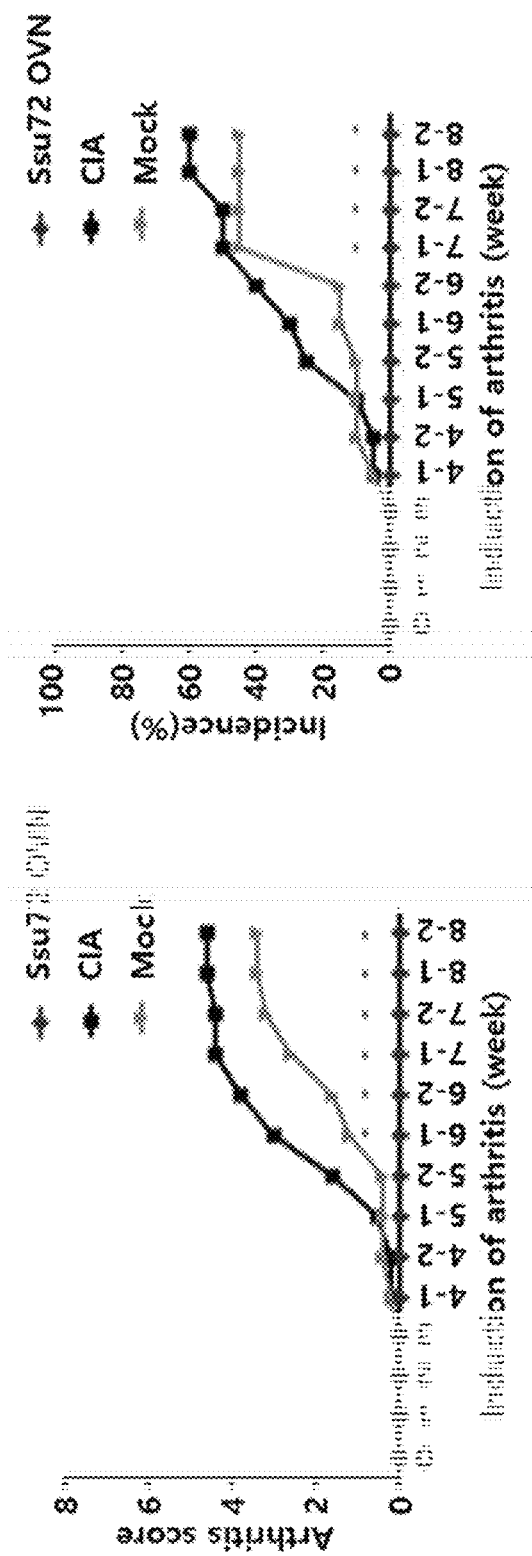
FIG. 6 illustrates the result of analyzing the degree of improvement of arthritis symptoms by injecting an Ssu72 overexpression expression vector into a mouse targeting rheumatoid arthritis mouse model.

As a result of the analysis, as illustrated in FIG. 6, the arthritis index of the arthritis mouse model injected with an Ssu72 overexpression vector was almost zero, indicating that a complete therapeutic effect can be induced, and that the arthritis-inducing environment did not induce arthritis in a mouse group injected with an Ssu72 overexpression vector.

Accordingly, through these results, the present inventors have found that Ssu72 has an activity that can effectively inhibit STAT3, and thus can effectively treat and prevent STAT3 mediated diseases such as rheumatoid arthritis, etc.

Example 5

Analysis of STAT3 Activation and IL-17 Expression Changes According to the Expression Inhibition of Ssu72

From the results of the above examples, the present inventors confirmed that when Ssu72 was overexpressed in cells, STAT3 phosphorylation was inhibited and IL-17 expression was decreased. In order to further demonstrate this, the inventors analyzed the STAT3 activity and the IL-17 expression changes by inhibition of Ssu72 expression using siRNA of Ssu72.

For this, siRNA (Santa Cruz, Cat. No: sc-76579) of Ssu72 was transduced in NIH3T3 cells, and then IL-6 (20 ng/ml) was stimulated by treating the cells for 30 minutes. The activation of STAT3, that is, the degree of phosphorylation, was confirmed by western blot and the degree of expression of IL-17 was analyzed by RT-PCR and luciferase assay. In addition, STAT3 activity and IL-17 expression changes were analyzed by western blot, RT-PCR, and luciferase assay after transduction of an Ssu72 mutant vector (phosphatase activity mutant of Ssu72) into NIH3T3 cells. At this time, the luciferase assay was performed after treating cells with IL-6 (20 ng/ml) for 15 minutes.

Figure 8:
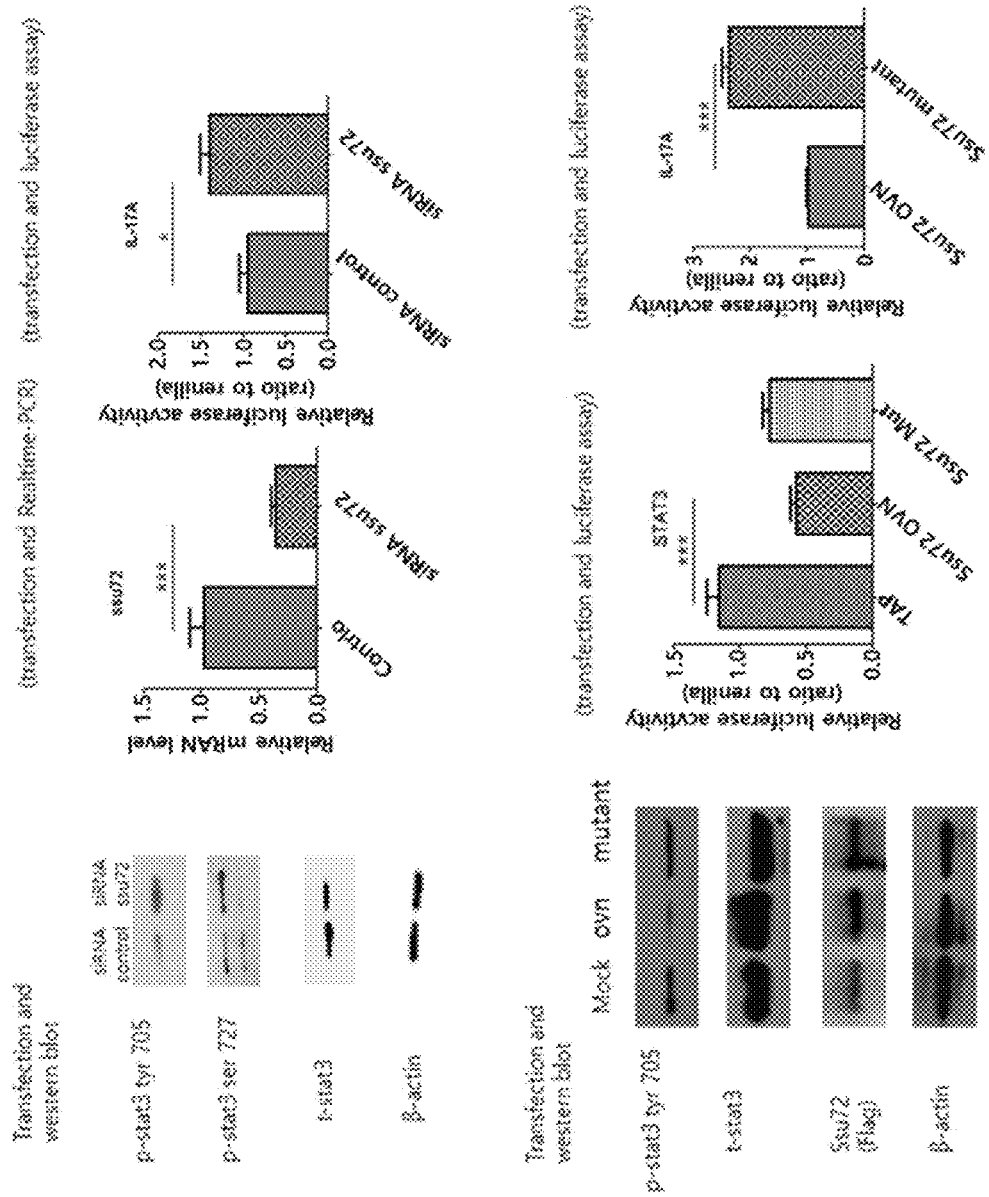
FIG. 8 illustrates the results of performing the degree of STAT3 phosphorylation and the expression degree of IL-17 cytokine for the group treated with Ssu72 siRNA and the group that is not treated in NIH3T3 cells by RT-PCR and western blot.

As a result of the analysis, as illustrated in FIG. 8, inhibition of Ssu72 expression using siRNA showed an increase in STAT3 phosphorylation and an increase in expression of IL-17 as compared with the control group that did not inhibit the expression of Ssu72.

In addition, STAT3 expression and IL-17 expression were increased as compared with a control group, as in the case of siRNA treatment, when the mutant that lost Ssu72 activity was expressed in the cells.

Example 6

Analysis of Expression Change of Inflammatory Mediators by Ssu72

The NIH3T3 cells were transduced into the Ssu72 overexpression vector prepared in the above example and treated with IL-6 (20 ng/ml) for 1 hour for cell stimulation. mRNA degree of the inflammatory mediators, IL-1beta, IL-6 receptor, IL-17A, IL-21, TBK1, and IKBKE was analyzed by RT-PCR and luciferase assay.

Figure 9:
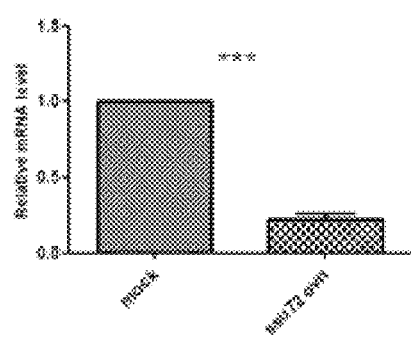
FIG. 9 illustrates the results of analyzing the degrees of expression inhibition of inflammatory mediators by RT-PCR and luciferase assay after introducing an Ssu72 overexpression vector in NIH3T3 cells and stimulating cells with IL-6.
Figure 9:
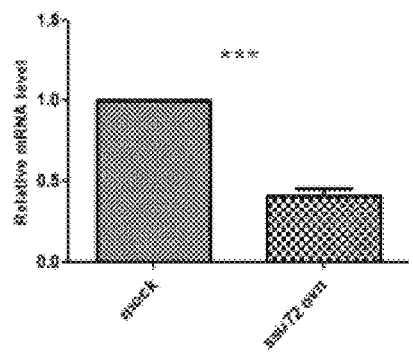
Figure 9:
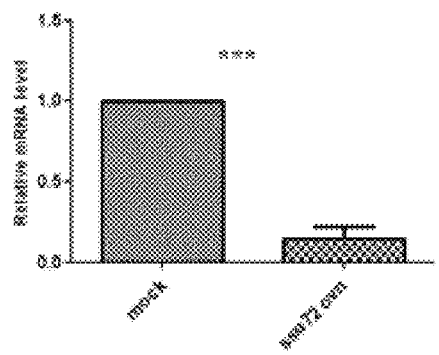
Figure 9:
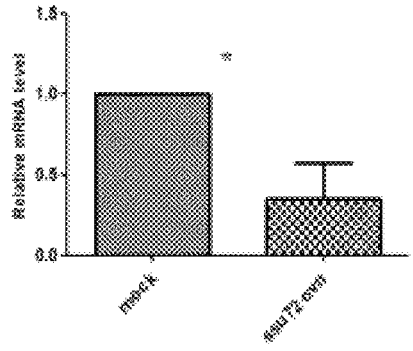
Figure 9:
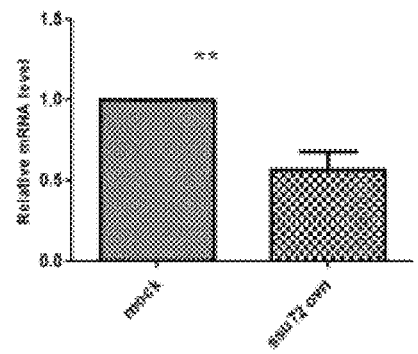
Figure 9:
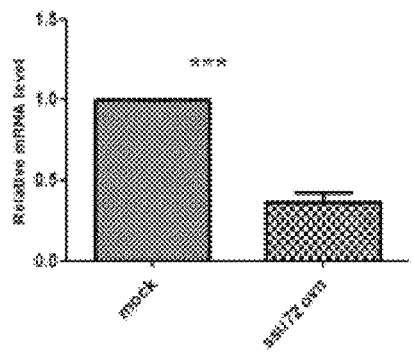

As a result of the analysis, as illustrated in FIG. 9, when Ssu72 was overexpressed, the mRNA of the inflammatory mediators, IL-1beta, IL-6 receptor, IL-17A, IL-21, TBK1, and IKBKE was significantly decreased as compared with a control group.

Accordingly, through these results, the present inventors have found that Ssu72 can inhibit the inflammatory response by inhibiting the expression of factors that mediate inflammatory.

Example 7

Analysis of Inhibitory Effect of Damage in Joint Tissue Using Ssu72 Gene and Inhibition of Production of Proinflammatory Cytokines In the collagen-induced mouse model prepared in the above example, mice injected with a vector overexpressing Ssu72 and mice of a control group injected with a vehicle vector were examined for the degree of immune cell penetration, proinflammatory cytokine expression, and osteoclast differentiation in each joint tissue.

Figure 10:
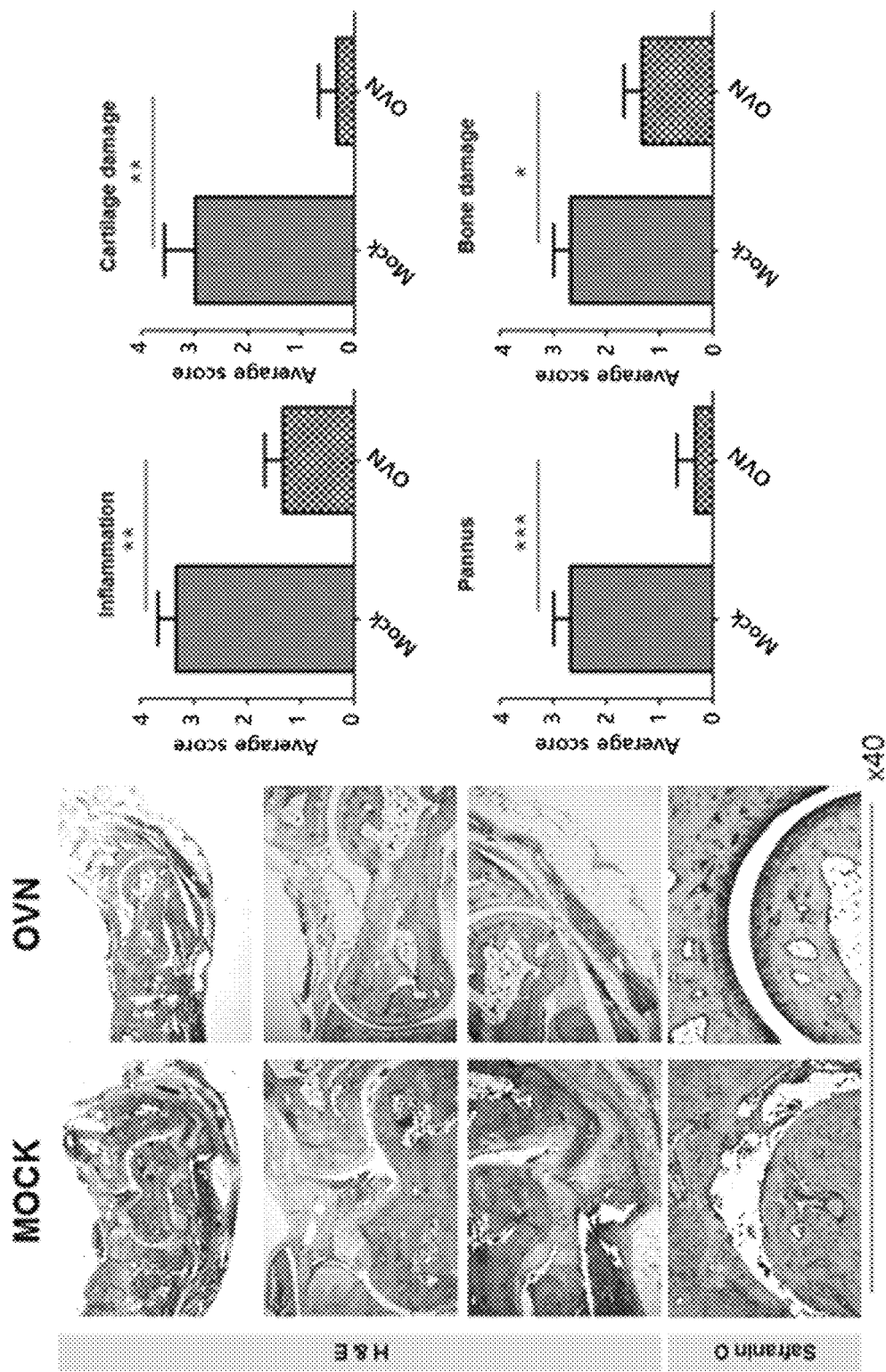
FIG. 10 illustrates the results of analyzing the inhibition of immune cell infiltration in joint tissues, damage of joints, development of pannus, and degree of bone damage after injecting an Ssu72 overexpression vector into a collagen-induced mouse group.

Immune cell penetration analysis was conducted for joint tissue using hematoxylene and eosin staining, and safranin o staining was performed. The analysis results showed that all of the degree of joint inflammation, the degree of joint damage, generation of pannus, and the degree of bone damage were significantly decreased in a group injected with an Ssu72 overexpression vector as compared with a control group (see FIG. 10).

Figure 11:
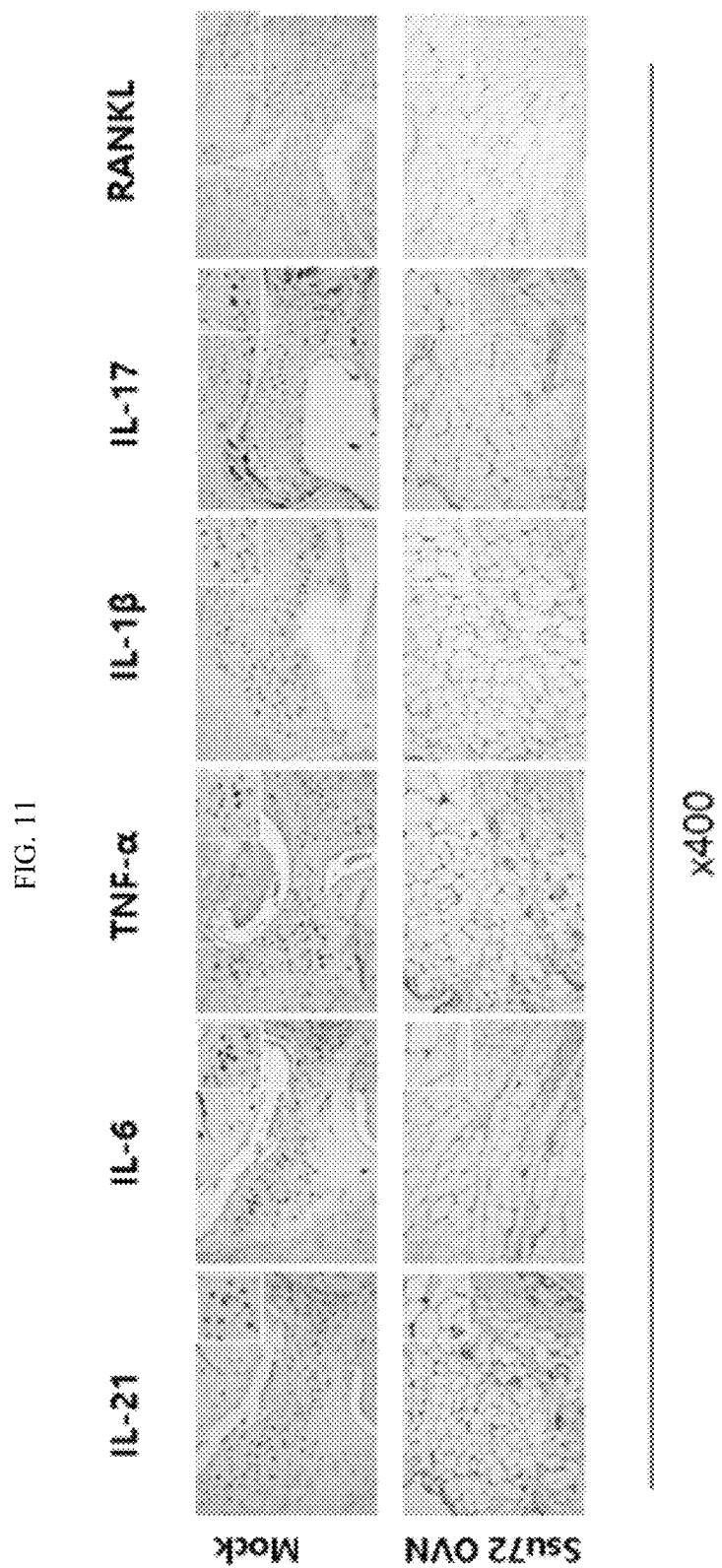
FIG. 11 is a photograph showing microscopic observation of the expression degree of proinflammatory cytokine in joint tissues after injecting an Ssu72 overexpression vector into a collagen-induced mouse group.

In addition, as a result of performing the expression degree of proinflammatory cytokines through immunochemical staining, as illustrated in FIG. 11, it was shown that the expression of the proinflammatory cytokines, IL-21, IL-6, TNF-α, IL-1beta, IL-17, and RANKL, was all inhibited.

Example 8

Analysis of Inhibitory Effect of Osteoclast Differentiation Using Ssu72 Gene

Joint tissue was obtained from the mouse model used in the above Example 7, and the expression levels of TRAP, RANKL, MMP-9, cathepsin K, and integrin-beta3, which are known as osteoclast differentiation factors, were confirmed by immunochemical staining.

Figure 12:
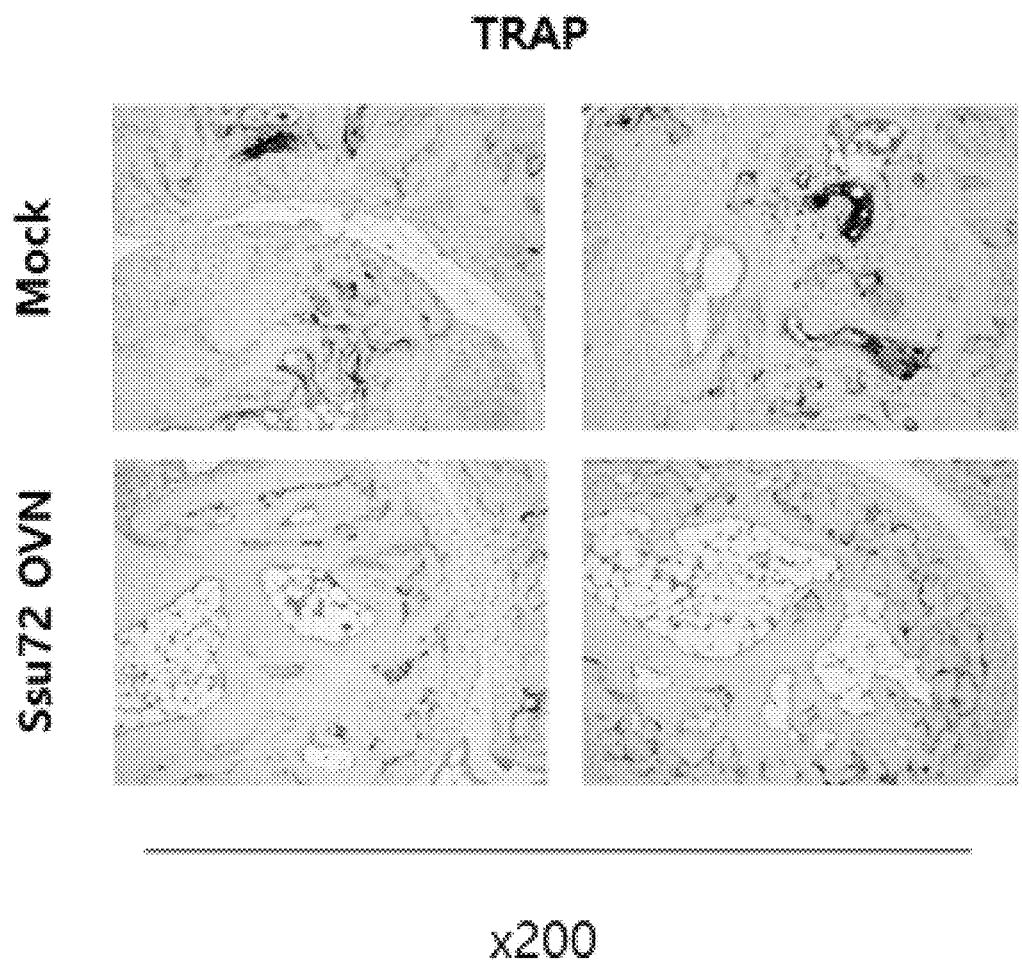
FIG. 12 is a photograph showing microscopic observation of the expression degree of TRAP, an osteogenic differentiation factor in joint tissues, after injecting an Ssu72 overexpression vector into a collagen-induced mouse group.
Figure 13:
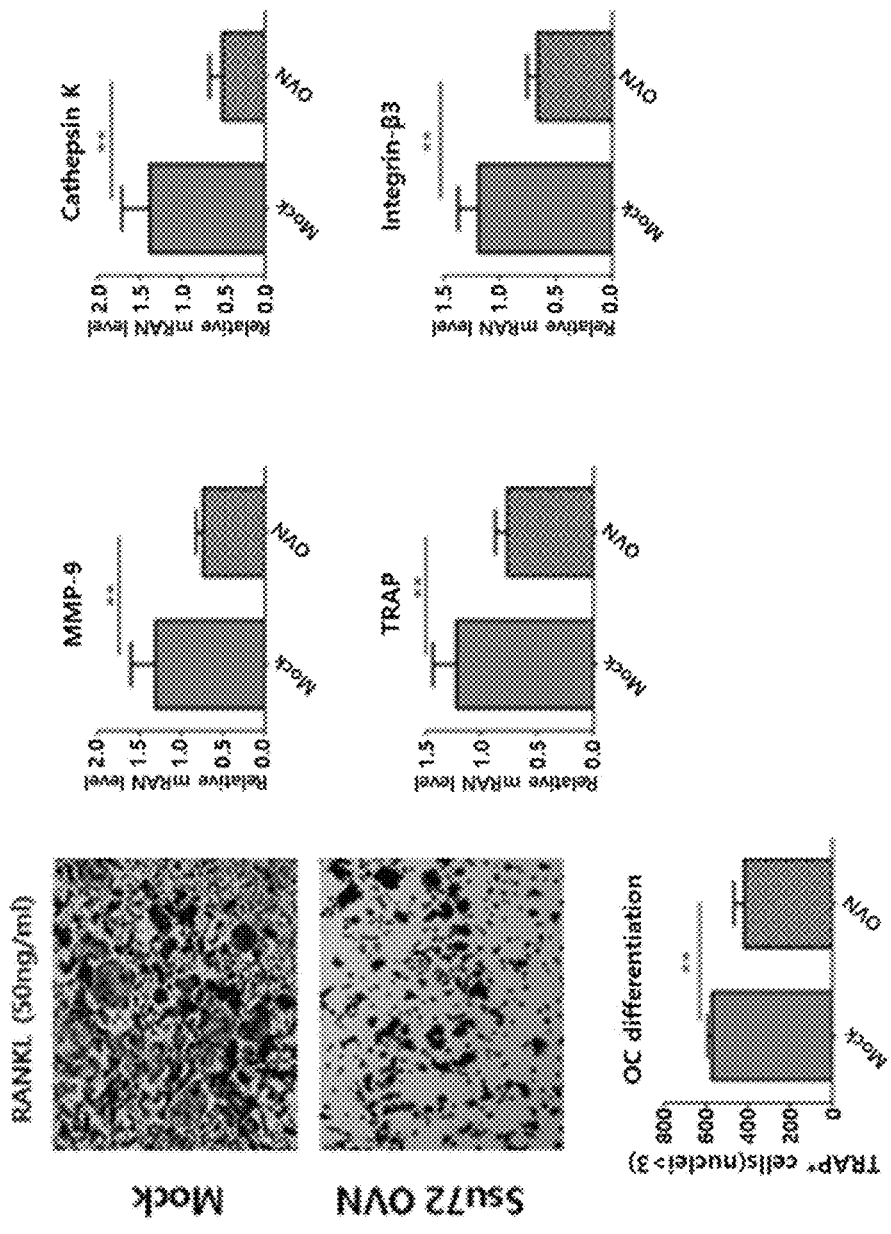
FIG. 13 illustrates the results of analyzing the expression degree of osteoclast differentiation inducing factors after injecting an Ssu72 overexpression vector into a collagen-induced mouse group

As a result of the analysis, the expression of TRAP, which is known as osteoclast differentiation factor in joint tissue, was inhibited in the Ssu72 overexpressed tissue as compared with the control group (Mock) not overexpressing Ssu72 (see FIG. 12) The expression of RANKL, MMP-9, cathepsin K, and integrin-beta3, which are factors inducing osteoclast differentiation, was also significantly decreased as compared with a control group, and the number of TRAP-positive cells was decreased, indicating that Ssu72 effectively inhibited osteoclast differentiation, and thus can be used as a therapeutic agent for bone diseases caused by osteoclasts (see FIG. 13).

Example 9

Analysis of Effects of Treg Increase and Th17 Inhibition by Ssu72 in Spleen Cells Spleen was obtained from the mice used in the above Example 7, and the change in the number of Treg cells and Th17 cells in spleen cells upon Ssu72 overexpression was analyzed by flow cytometry.

Figure 14:
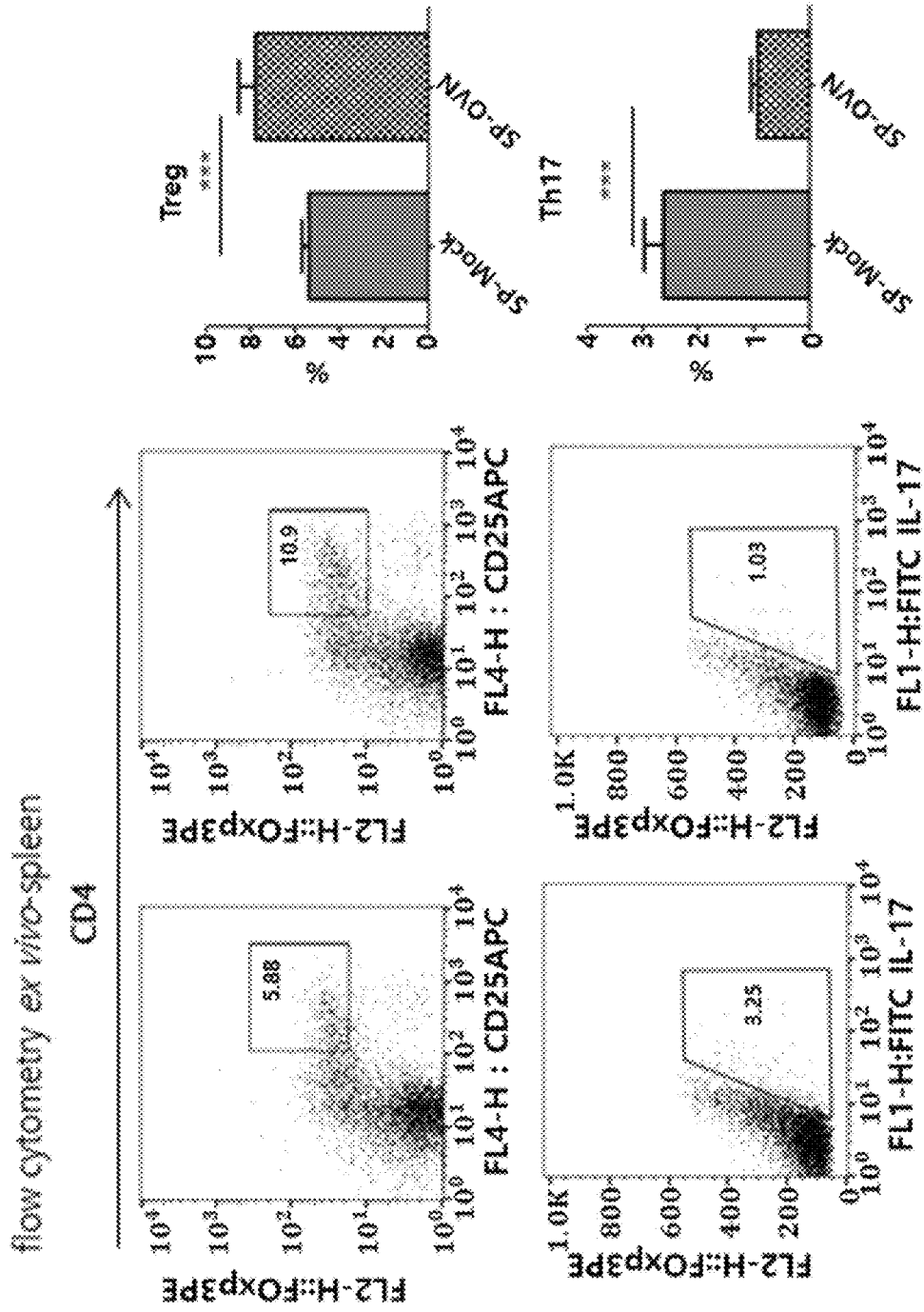
FIG. 14 illustrates the results of analyzing the number of Th17 cells and Treg cells, which are pathogenic cells, by flow cytometer, after injecting an Ssu72 overexpression vector into a collagen-induced mouse group and isolating splenocyte cells from the mice.
Figure 15:
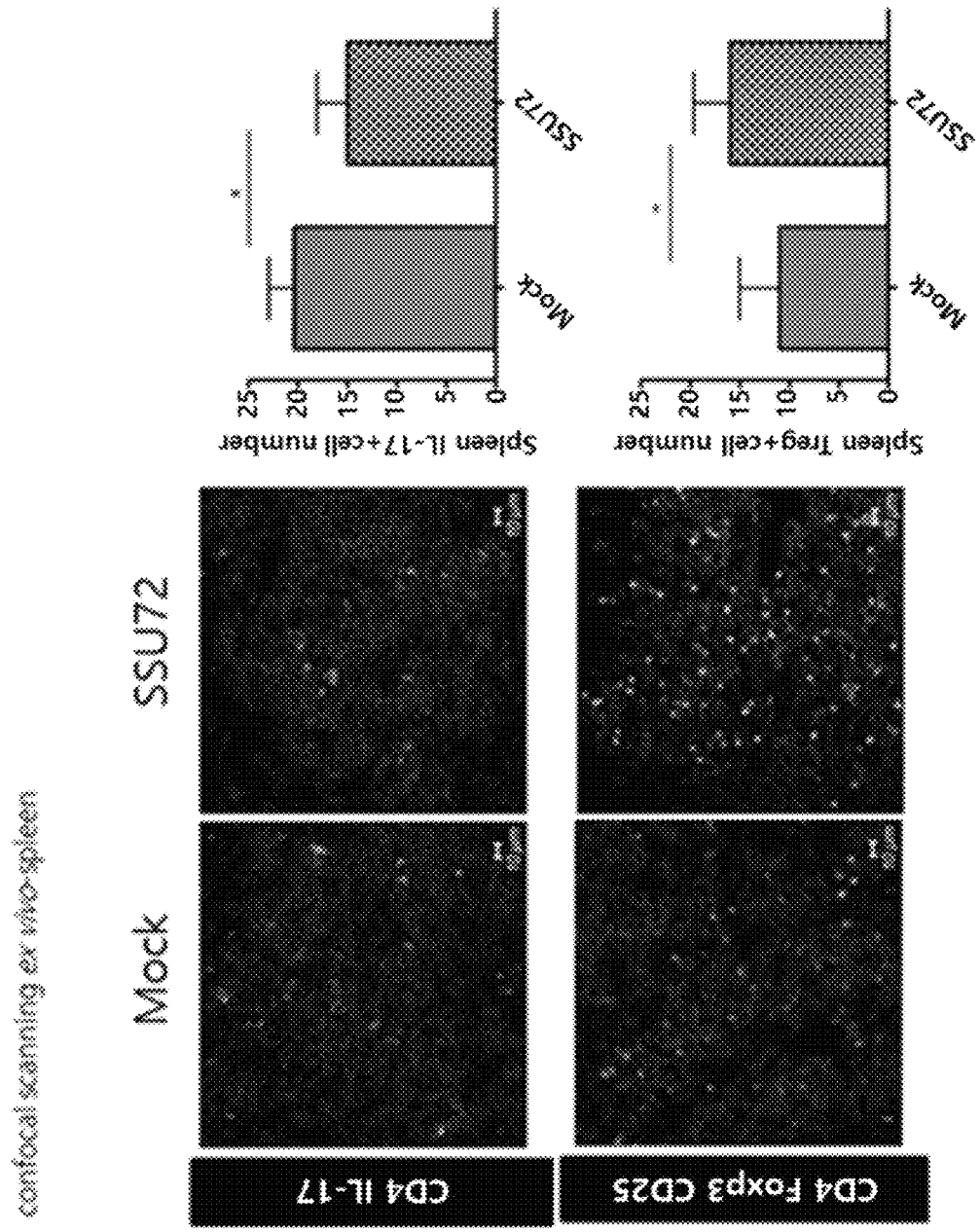
FIG. 15 is a photograph showing the results of observing Th17 cells and Treg cells by a confocal microscope after injecting an Ssu72 overexpression vector into a collagen-induced mouse group and isolating splenocyte cells from the mice.
Figure 16:
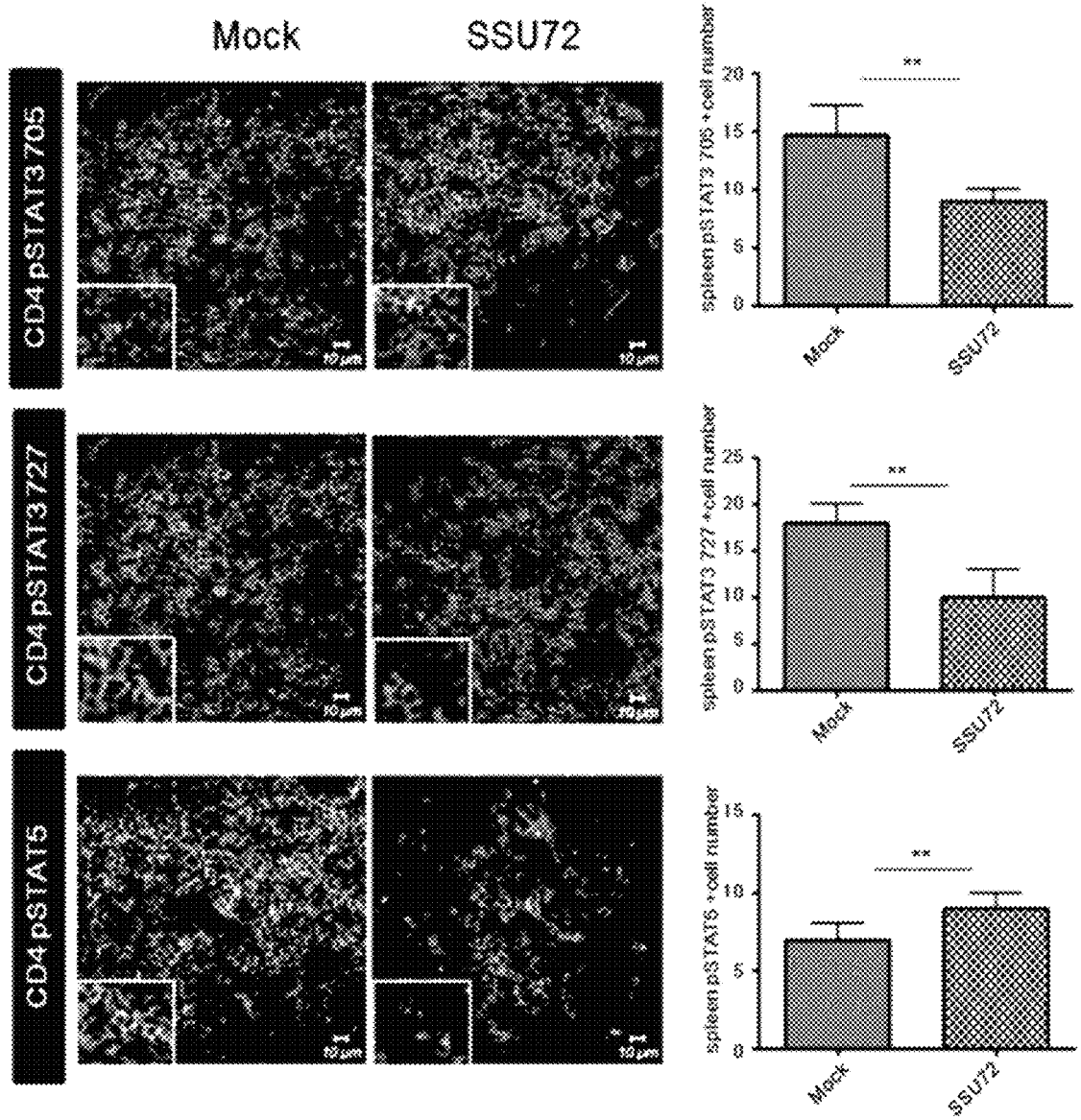
FIG. 16 is a photograph showing the results of observing the expression degree of p-STAT3 by a confocal microscope after injecting an Ssu72 overexpression vector into a collagen-induced mouse group and isolating splenocyte cells from the mice.
Figure 17:
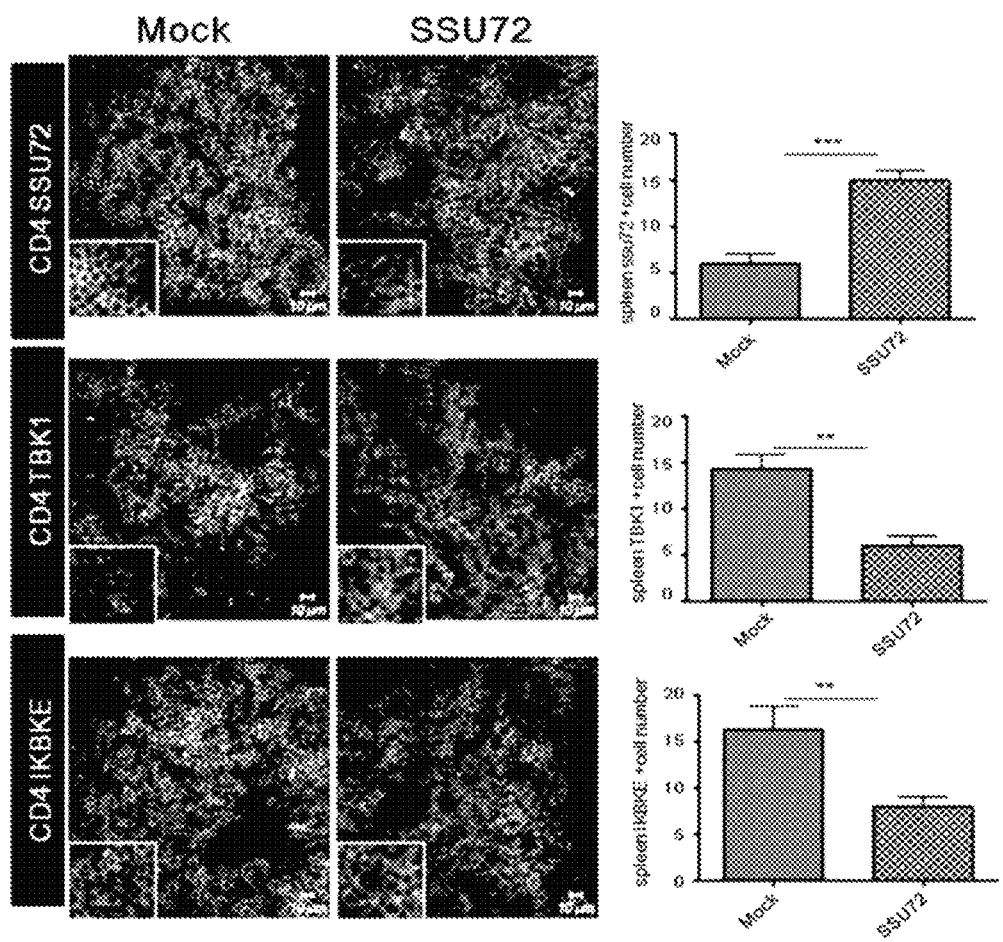
FIG. 17 is a photograph showing the results of observing the expression degree of inflammatory mediators by a confocal microscope after injecting an Ssu72 overexpression vector into a collagen-induced mouse group and isolating splenocyte cells from the mice.

As a result of the analysis, as illustrated in FIG. 14, Treg cells, which are immunoregulatory T cells, showed an increase in cell number during Ssu72 overexpression (5.88→10.9). On the other hand, Th17 cells, which are pathogenic cells, showed a decrease in cell number (3.25→1.03). These results suggest that Ssu72 has a function of regulating immune cells in spleen cells, and it is possible to increase the number of Treg cells having the immunoregulatory ability and decrease the number of Th17 cells.

In addition, these results were also confirmed by confocal microscope observation. In spleen cells of a group overexpressing Ssu72 and spleen cells of a control group not overexpressing Ssu72, 1) CD4 Foxp CD25 and CD4 IL-17 positive cells were observed, 2) CD4 pSTAT3 705, CD4 pSTAT3 727, CD4 pSTAT5, and CD4 pSTAT3 were observed, and 3) the cells positive on the inflammatory mediators such as CD4 TBK1 and CD4 IKBKE were observed.

As a result of the analysis, according to FIGS. 15 to 17, 1) when Ssu72 was overexpressed, the number of Treg cells, which are Foxp-positive cells, was increased as compared with a control group, whereas the number of Th17 cells was decreased. 2) The number of visible cells of phosphorylated STAT3 705 and phosphorylated STAT3 727 was decreased when Ssu72 was overexpressed, whereas the number of cells of pSTAT5 was increased. In addition, 3) the number of TBK1, IKBKE positive cells, which are inflammatory mediators, was decreased when Ssu72 was overexpressed.

Example 10

Analysis of Effects of Treg Increase and Th17 Inhibition by Ssu72 in Lymph Nodes In order to confirm whether there is a change in the number of Treg cells and the number of Th17 cells by Ssu72 overexpression in lymph nodes, the present inventors extracted lymph nodes from the mouse models used in the above examples. Then, the number of Treg cells and the number of Th17 cells were confirmed by flow cytometry.

Figure 18:
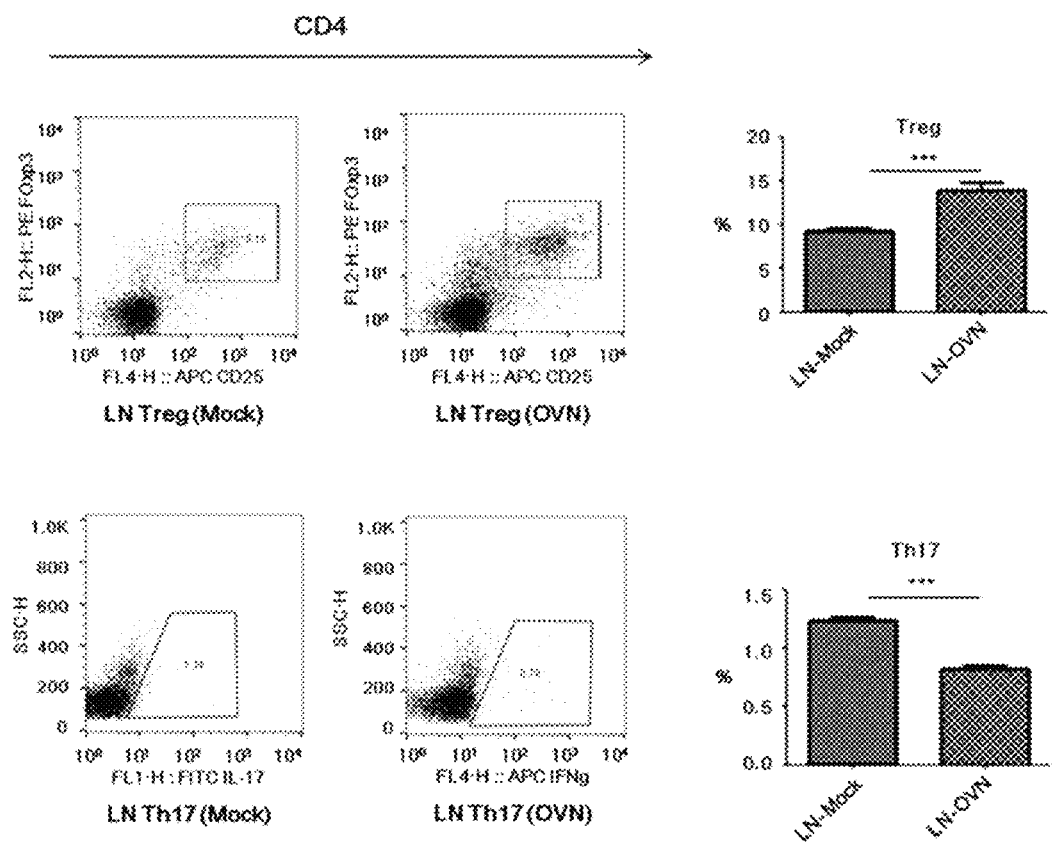
FIG. 18 illustrates the results of analyzing Th17 cells and Treg cells in the lymph nodes by a flow cytometer after injecting an Ssu72 overexpression vector into a collagen-induced mouse group and isolating the lymph nodes from the mice.

As a result of the analysis, as illustrated in FIG. 18, in the lymph nodes, the number of Treg cells, which are immunoregulatory T cells, was increased by Ssu72 overexpression, whereas the number of Th17 cells was decreased as in the spleen cells.

Example 11

Analysis of Inflammatory Mediator Expression Changes by Ssu72 in Lymph Nodes

The expression changes of inflammatory mediators according to Ssu72 overexpression in the lymph nodes of the mice used in Example 10 were analyzed by RT-PCR.

Figure 19:
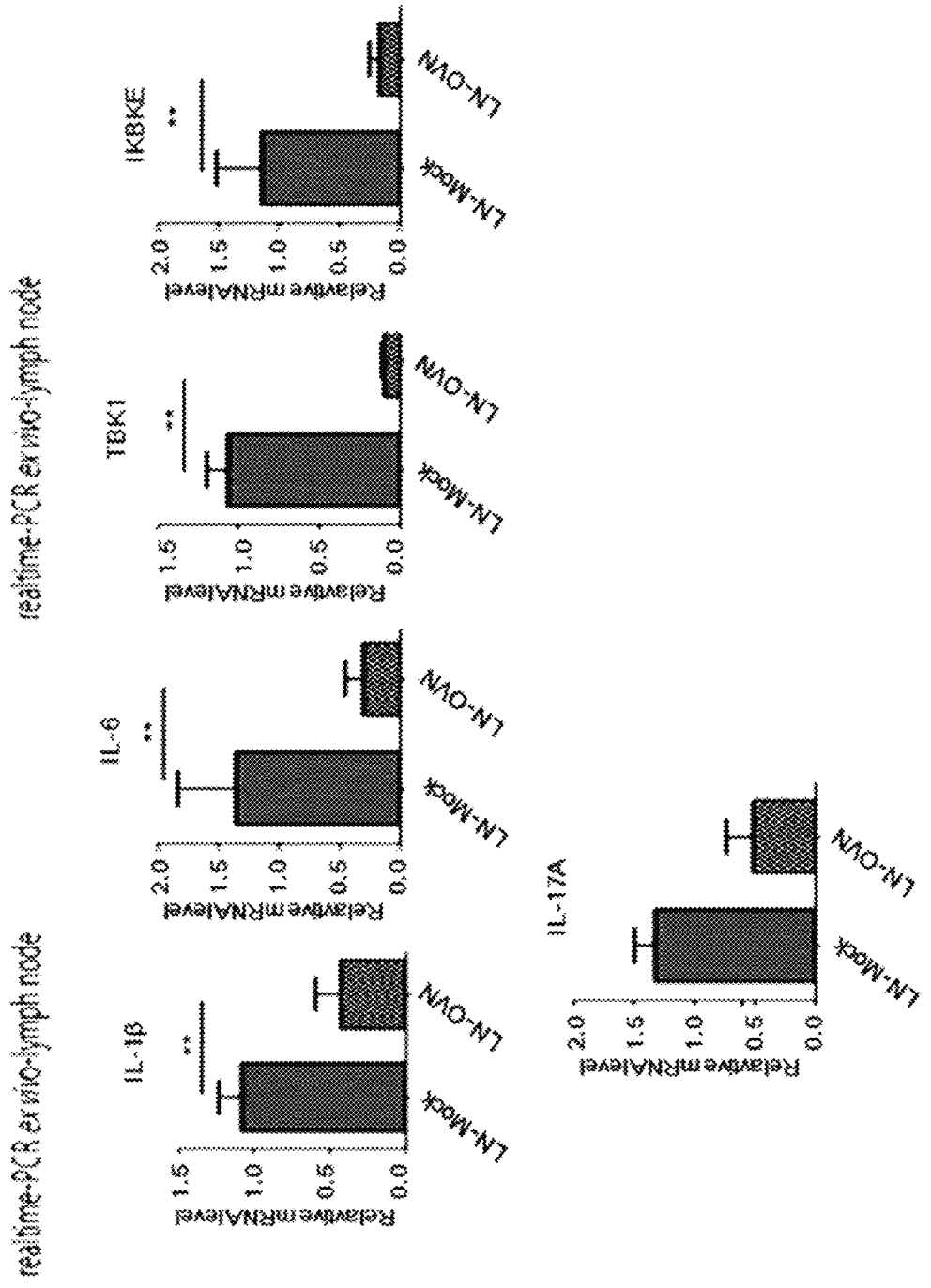
FIG. 19 illustrates the results of analyzing the expression changes of inflammatory mediators in the lymph nodes after injecting an Ssu72 overexpression vector into a collagen-induced mouse group and isolating the lymph nodes from the mice.

As a result of the analysis, as illustrated in FIG. 19, when Ssu72 was also overexpressed in the lymph nodes, the expression of the inflammatory mediators, IL-1 beta, IL-6, IL-17A, TBK1, and IKBKE, was decreased.

Example 12

Inhibitory Effect of Germinal Center B Cell Expression by Ssu72 in Spleen and Lymph Node The spleen and lymph nodes were separately extracted from mice used in the above examples, i.e., a mouse group injected with an ssu72 overexpression vector into collagen-induced arthritis mice, and a control group. The expression degrees of germinal center B cells, which are pathogenic cells in the spleen and lymph node, were analyzed by flow cytometer.

Figure 20:
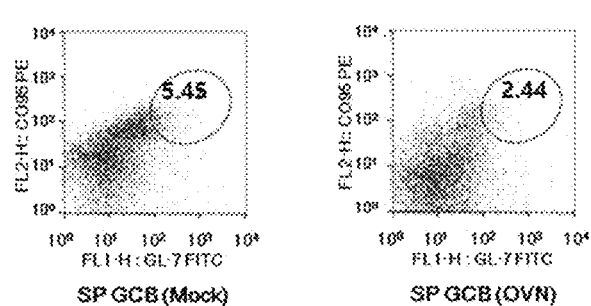
FIG. 20 illustrates the results of analyzing the degree of expression inhibition of germinal center B cells, which are pathogenic cells, by a flow cytometer after injecting an Ssu72 overexpression vector into a collagen-induced mouse group and isolating splenocytes and lymph nodes from the mice.
Figure 20:
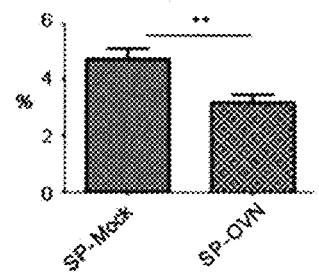
Figure 20:
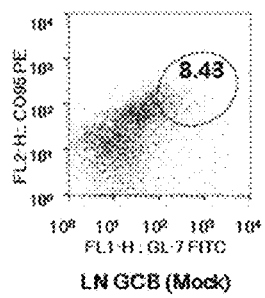
Figure 20:
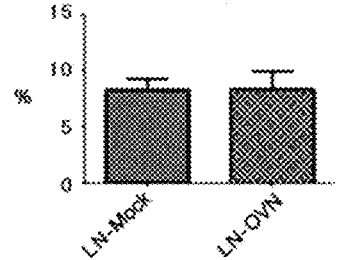

As a result of the analysis, as illustrated in FIG. 20, germinal center B cells, which are pathogenic cells, showed a decrease in cell number by overexpression of Ssu72.

Figure 21:
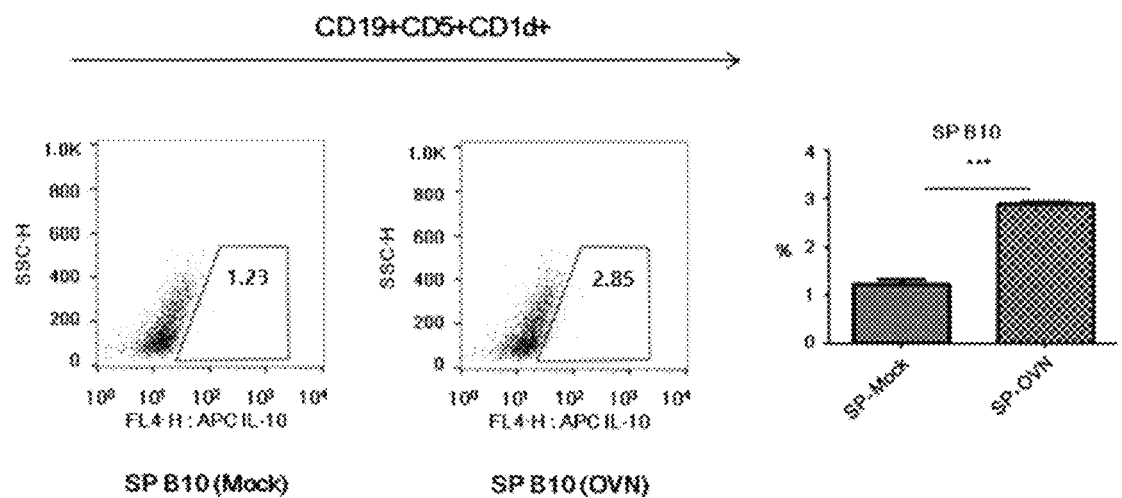
FIG. 21 illustrates the results of analyzing the expression degree of B10 cells showing immunosuppressive ability by a flow cytometer after injecting an Ssu72 overexpression vector into a collagen-induced mouse group and isolating splenocytes and lymph nodes from the mice.
Figure 21:
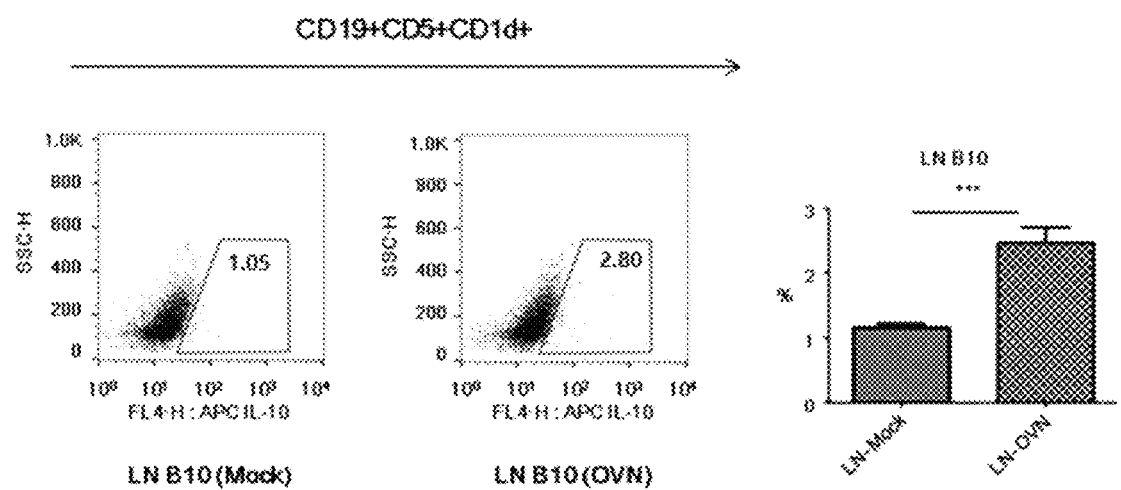

In addition, the present inventors analyzed the expression degree of B10 cells showing inflammatory response inhibitory ability through flow cytometer. As illustrated in FIG. 21, B10 cells showed an increase in cell number upon Ssu72 overexpression in both spleen and lymph node.

Example 13

The Inhibitory Effect of Autoantibodies of Ssu72

Serum was obtained from mice injected with an Ssu72 overexpression vector in collagen-induced arthritis mice and control group mice injected with a mock vector, and the expression degree of autoantibodies in serum was analyzed by ELISA. In addition, B cells expressing IL-10 in spleen cells and CD4+p-STAT3+IL-17+ cells were observed through a confocal microscope.

Figure 22:
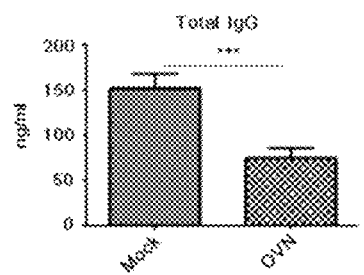
FIG. 22 illustrates the results of confirming the expression degree of autoantibodies in serum by isolating serum from the mice after injecting an Ssu72 overexpression vector into a collagen-induced mouse group, and illustrates the results of confirming the expression degree of B cells expressing IL-10 in splenocytes by isolating splenocytes from the mice.
Figure 22:
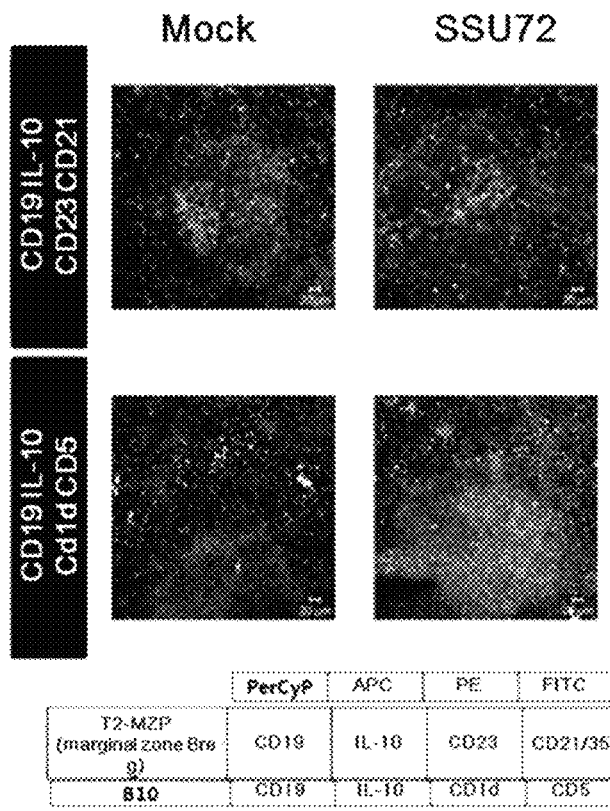
Figure 23:
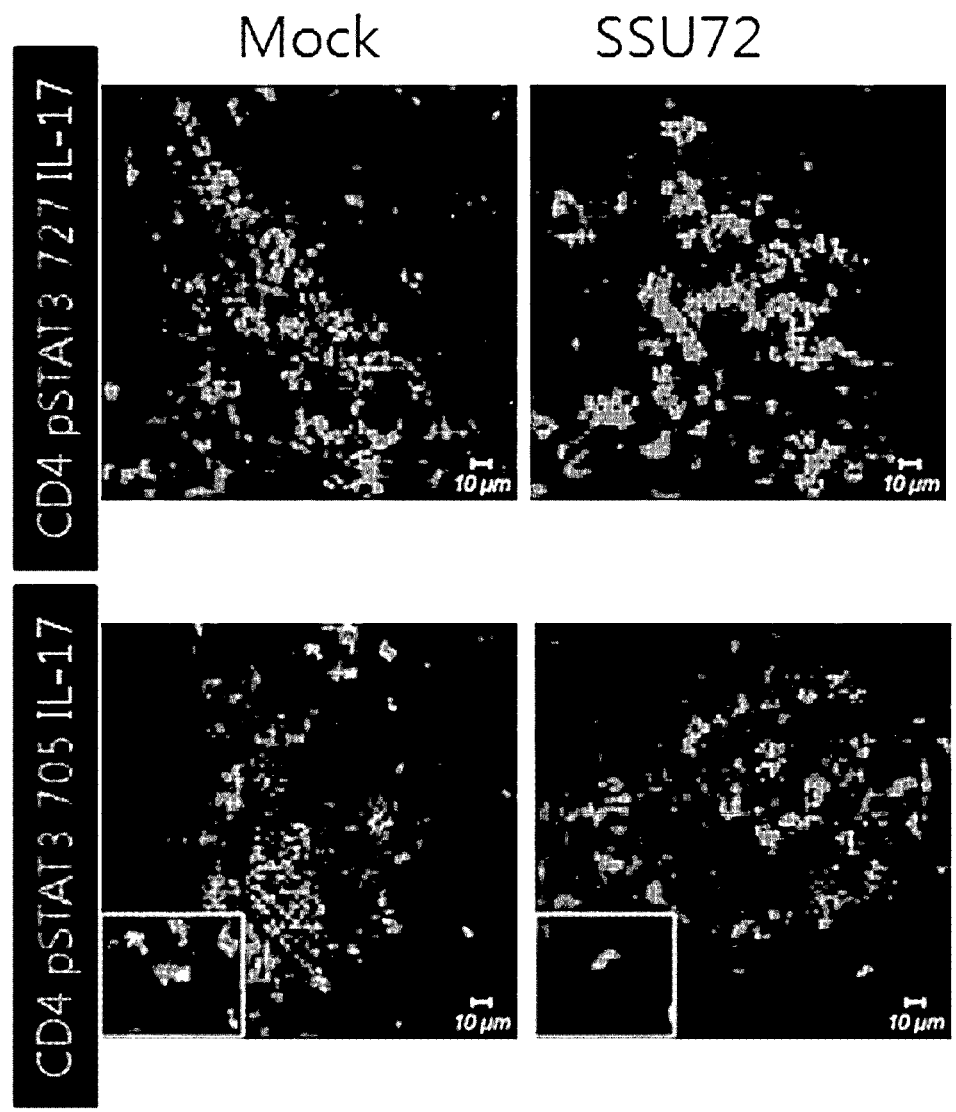
FIG. 23 is a photograph showing the results of observing the expression degree of CD4+p-STAT3+IL-17+ cells in splenocytes by a confocal microscope after injecting an Ssu72 overexpression vector into a collagen-induced mouse group and isolating the splenocyte from the mice.

As a result of the analysis, as illustrated in FIG. 22 and FIG. 23, when Ssu72 was overexpressed, the expression of autoantibodies (IgG) was decreased and the expression of B cells expressing IL-10 in spleen cells was increased (FIG. 22), whereas CD4+p-STAT3+IL-17+ cells were decreased (FIG. 23).

Accordingly, through these results, the present inventors have found that Ssu72 inhibits the expression of autoantibodies and is used as a therapeutic agent for autoimmune diseases through regulation of IL-10 expressing B cells (increase) and IL-17 cells (inhibition) having an immunoregulatory ability.

Example 14

Analysis of Regulation of Th1 Cell, Th2 Cell, and Marginal Zone B Cell Expression by Ssu72 Overexpression in Spleen Cells Furthermore, the present inventors extracted spleen and lymph node from mice injected with an Ssu72 overexpression vector in collagen-induced arthritis mice and control group mice injected with a mock vector and analyzed the number of Th1 cells, which are pathogenic cells in the spleen and lymph nodes, Th2 cells having anti-inflammatory activity, and marginal zone B cells by a flow cytometer.

Figure 24:
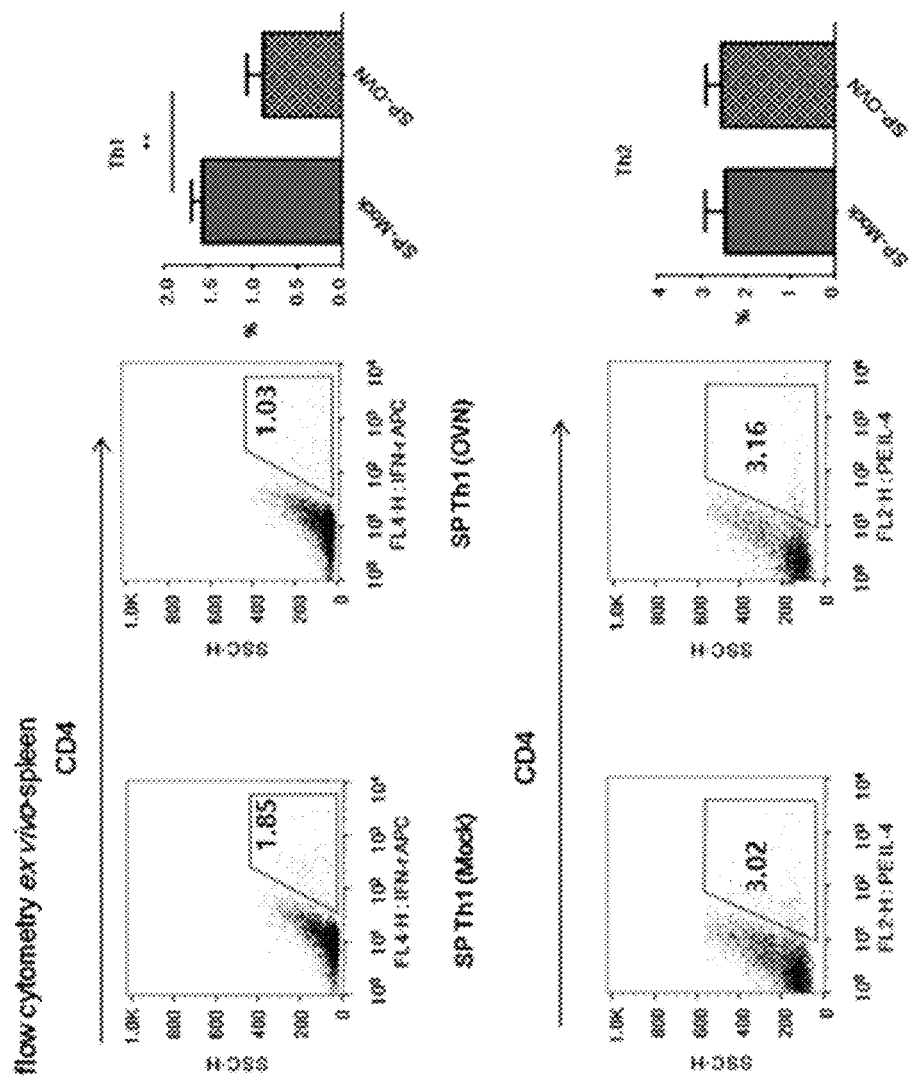
FIG. 24 illustrates the results of analyzing the degree of expression inhibition of Th1 cells, which are pathogenic cells, in splenocytes by a flow cytometer after injecting an Ssu72 overexpression vector into a collagen-induced mouse group and isolating the splenocytes from the mice.
Figure 25:
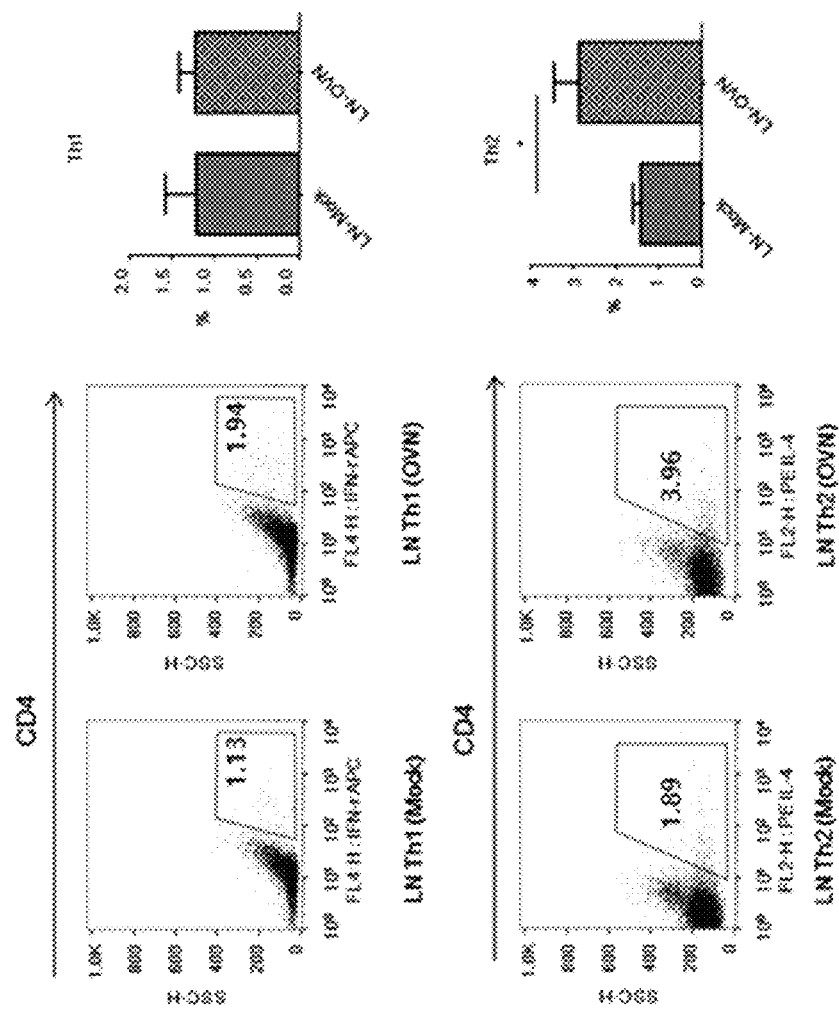
FIG. 25 illustrates the results of analyzing the degree of expression enhancement of Th2 cells with anti-inflammatory action in a lymph node by a flow cytometer after injecting an Ssu72 overexpression vector into a collagen-induced mouse group and isolating the lymph nodes from the mice.
Figure 26:
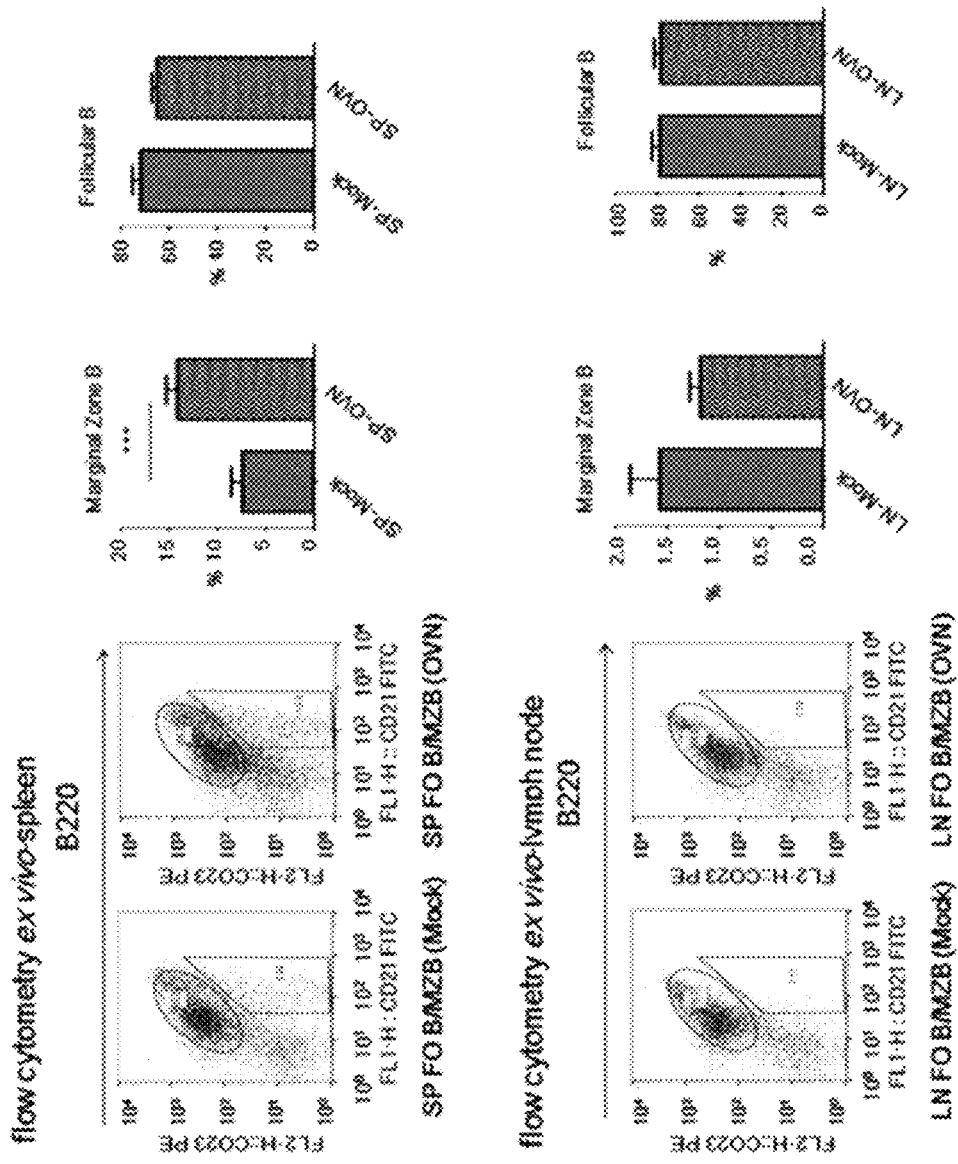
FIG. 26 illustrates the results of analyzing the expression degree of marginal zone B cells having anti-inflammatory action in a lymph node isolated from mice by a flow cytometer after injecting an Ssu72 overexpression vector into a collagen-induced mouse group.

As a result of the analysis, as illustrated in FIG. 24, the expression of Th1 cells, which are pathologic cells in spleen cells, was inhibited in a group injected with an Ssu72 overexpression vector as compared with a control group, and there was no significant change in the expression of Th2 cells in spleen cells. In addition, the expression of Th2 cells having anti-inflammatory activity in the lymph nodes was increased when Ssu72 was overexpressed (see FIG. 25). Marginal zone B cells with anti-inflammatory activity exhibited different levels of expression in the spleen and lymph nodes. In the spleen, expression degree was increased in Ssu72 overexpression and decreased in lymph node (see FIG. 26).

From the above results, the present inventors have found that Ssu72 of the present disclosure can be used as a gene therapeutic agent and a protein therapeutic agent for the treatment of immune diseases, particularly autoimmune diseases.

The present disclosure has been described mainly with reference to the preferred embodiments. It will be understood by a person having ordinary knowledge in the technical field to which the present disclosure pertains that the present disclosure may be embodied in various other forms without departing from the spirit or essential characteristics thereof. Therefore, the disclosed examples should be considered in an illustrative sense rather than a restrictive sense. The scope of the present disclosure is defined by the claims rather than by the foregoing description, and all differences within the scope of equivalents thereof should be construed as being included in the present invention.

The invention claimed is:

1. A method for inhibiting a STAT3 activity, comprising administering to a subject in need thereof a Ssu72 protein.

2. The method according to claim 1, wherein the STAT3 activity is induced by IL-6.

3. The method according to claim 1, wherein the subject suffers from rheumatoid arthritis.

* * * * *